(12) United States Patent
Cui et al.

(10) Patent No.: US 10,737,991 B2
(45) Date of Patent: Aug. 11, 2020

(54) PROCESS FOR PRODUCING LIGHT OLEFINS

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Shouye Cui, Beijing (CN); Youhao Xu, Beijing (CN); Jingchuan Yu, Beijing (CN); Minggang Li, Beijing (CN); Baoning Zong, Beijing (CN); Jinlian Tang, Beijing (CN); Xin Wang, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 0 days.

(21) Appl. No.: 15/520,729

(22) PCT Filed: Oct. 20, 2015

(86) PCT No.: PCT/CN2015/000705
§ 371 (c)(1),
(2) Date: Apr. 20, 2017

(87) PCT Pub. No.: WO2016/061906
PCT Pub. Date: Apr. 28, 2016

(65) Prior Publication Data
US 2017/0305815 A1    Oct. 26, 2017

(30) Foreign Application Priority Data

Oct. 20, 2014 (CN) .......................... 2014 1 0559920

(51) Int. Cl.
*C07C 5/48* (2006.01)
*C07C 1/20* (2006.01)
(Continued)

(52) U.S. Cl.
CPC ............... *C07C 5/48* (2013.01); *B01J 21/02* (2013.01); *B01J 29/06* (2013.01); *B01J 29/40* (2013.01);
(Continued)

(58) Field of Classification Search
CPC ........... C07C 5/48; C07C 11/00; C07C 11/02; C07C 11/04; C07C 11/06
See application file for complete search history.

(56) References Cited

U.S. PATENT DOCUMENTS 7,138,558 B2 * 11/2006 Lacijan ................... B01J 4/002
585/640
7,439,414 B2 * 10/2008 Miller ..................... B01J 38/00
502/21
(Continued)

FOREIGN PATENT DOCUMENTS

CN      101260013 A      9/2008
CN      101348404 A      1/2009
(Continued)

OTHER PUBLICATIONS

Kazakhstan Patent Office, "Office Action" for 2017/0412.1, dated Aug. 16, 2018.
(Continued)

*Primary Examiner* — Youngsul Jeong
(74) *Attorney, Agent, or Firm* — Novick, Kim & Lee, PLLC; Allen Xue

(57) ABSTRACT

Disclosed is a process for producing light olefins, the process comprising: continuously contacting an oxygen-containing compound raw material with catalyst to have a
(Continued)

dehydration reaction so as to prepare low-carbon alkene, the reaction pressure P of the dehydration reaction being 1-2 MPa, and the weight hourly space velocity H of the dehydration reaction being 15-50 $h^{-1}$. The process of preparing light olefins has a simple and continuous operation process, reduces investment, greatly increases production of light olefins and has a high safety.

14 Claims, 7 Drawing Sheets

(51) Int. Cl.
    *C07C 4/06*     (2006.01)
    *B01J 29/90*     (2006.01)
    *B01J 29/06*     (2006.01)
    *B01J 38/12*     (2006.01)
    *B01J 29/40*     (2006.01)
    *B01J 29/85*     (2006.01)
    *B01J 21/02*     (2006.01)
    *C07C 11/00*     (2006.01)
    *B01J 8/18*     (2006.01)
    *F28D 21/00*     (2006.01)

(52) U.S. Cl.
    CPC ............... *B01J 29/85* (2013.01); *B01J 29/90* (2013.01); *B01J 38/12* (2013.01); *C07C 1/20* (2013.01); *C07C 4/06* (2013.01); *C07C 11/00* (2013.01); *B01J 8/1872* (2013.01); *B01J 29/061* (2013.01); *C07C 2529/40* (2013.01); *C07C 2529/85* (2013.01); *F28D 2021/0022* (2013.01); *Y02P 20/52* (2015.11); *Y02P 20/584* (2015.11); *Y02P 30/42* (2015.11)

(56) References Cited

U.S. PATENT DOCUMENTS

| 8,304,594 | B2 * | 11/2012 | Xie | ........................... C07C 1/20 585/638 |
| 2005/0203326 | A1 * | 9/2005 | Miller | ..................... B01J 8/006 585/640 |

FOREIGN PATENT DOCUMENTS

| DE | 3524890 A | 1/1986 |
| EA | 201270737 A1 | 2/2013 |
| EA | 020083 B1 | 8/2014 |
| WO | 0160770 A1 | 8/2001 |
| WO | 2012167708 A1 | 12/2012 |
| WO | 2013091335 A1 | 6/2013 |
| WO | WO-2014207134 A1 * | 12/2014 ............... C07C 1/20 |

OTHER PUBLICATIONS

European Patent Office, "Supplementary European Search Report" for EP 15852702, dated May 29, 2018.

* cited by examiner

PROCESS FOR PRODUCING LIGHT OLEFINS

TECHNICAL FIELD

The present invention relates to a process for producing light olefins from oxygen-containing compound feedstock. Specifically, the present invention relates to a process for increasing the output of light olefins in a process for producing light olefins from oxygen-containing compound feedstock.

BACKGROUND OF THE INVENTION

Lower olefins (C2-C4 olefins) are the fundamental starting materials for the organic chemical industry, and have an important role in the modern petroleum and chemical industry. On the whole, the process for producing light olefins may be divided into two general classes, i.e. the traditional petroleum way and the novel non-petroleum way. Since the 1910s, the world began to investigate the process for producing light olefins from non-petroleum resources (especially the oxygen-containing compound feedstock) and made some progresses.

The process of producing light olefins through the dehydration reaction of the oxygen-containing compound produces a certain amount of water as by-product except the hydrocarbon products, for example, about 44% of the hydrocarbon products from methanol and about 46% of the hydrocarbon products from ethanol. It is known that the reaction producing light olefins with the oxygen-containing compound feedstock is a reaction in which the amount of molecules increases, and therefore the lower reaction pressure is favorable for the chemical equilibrium to proceed toward the production of light olefins. Therefore, upon producing light olefins, in order to obtain a desired yield of light olefins, the prior art generally uses a lower reaction pressure. This lower reaction pressure (typically 0.1-0.3 MPa) directly results in that if desired to increase the throughput of the oxygen-containing compound feedstock in order to increase the output of light olefins, the prior art will therefore have to increase the size or amount of the reactor so as to maintain the yield of light olefins at an acceptable level. Obviously, this will accordingly increase the investment and maintenance cost of the plant.

In the process for producing light olefins according to the prior art, in order to guarantee a continuous production process, the catalyst is circulated between the reactor and the regenerator. In order to facilitate the circulation, the reactor and the regenerator are generally operated at the substantially same pressure. Under this situation, the reactor is in a hydrocarbon atmosphere, and the regenerator is in an oxygen-containing atmosphere. If the reactor and the regenerator are not well segregated, there will be a large potential safety hazard.

In addition, a cyclone similar to that used in the catalytic cracking unit is widely used in the plant for producing light olefins according to the prior art. Therefore, it is inevitable for the catalyst natural loss during the production, in particular in case that the catalyst fine powder having a particle size of less than 20 microns becomes more and more in the catalyst. This will have a detrimental effect on the subsequent product separation, and will be adverse for the catalyst to be reused.

SUMMARY OF THE INVENTION

The purpose of the present invention is to provide a process for producing light olefins, which process overcomes the foresaid disadvantages in the prior art and is capable of directly utilizing the existing reactor and easily achieving the purpose of increasing the output of light olefins.

The present inventors have surprisingly found through an industrious investigation that if increasing the reaction pressure and correspondingly and simultaneously and correspondingly increasing the WHSV of the oxygen-containing compound feedstock, the yield of light olefin can be maintained at a level which is comparable to or even higher than that of the prior art, instead decreases as previously expected in the prior art, resulting in that for an existing reactor, the technical solution of increasing the reaction pressure and the WHSV of the reactor according to the present invention will remarkably increase the throughput of the oxygen-containing compound feedstock in the reactor and accordingly increase the output of light olefins (i.e. increase the production of light olefins). This finding made by the present inventions breaks through the routine knowledge of those skilled in the art, and therefore accomplish the present invention based on this finding.

Specifically speaking, the present invention relates to the following contents.

1. A process for producing light olefins (or increasing the output of light olefins), wherein in the process for producing light olefins by continuously contacting an oxygen-containing compound feedstock and a catalyst to conduct a dehydration reaction, the reaction pressure P of the dehydration reaction is 0.5-10 MPa, preferably 0.75-3.5 MPa, more preferably 0.8-3 MPa, most preferably 1-2 MPa, the weight hourly space velocity H of the dehydration reaction is 7-250 $h^{-1}$, preferably 8-150 $h^{-1}$, more preferably 10-100 $h^{-1}$, more preferably 15-80 $h^{-1}$, most preferably 15-50 $h^{-1}$.

2. The process according to any of previous aspects, wherein during the dehydration reaction, H and P satisfy a mathematical function of H=f(P), which is a strictly increasing function, wherein P (unit: MPa) is in the interval [0.55, 10.0], preferably in the interval [0.75, 3.5], more preferably in the interval [0.8, 3.0], most preferably in the interval [1.0, 2.0], H (unit: $h^{-1}$) is in the interval [7, 250], preferably in the interval [8, 150], more preferably in the interval [10, 100], more preferably in the interval [15, 80], most preferably in the interval [15, 50].

3. The process according to any of previous aspects, comprising the following steps:

continuously contacting the oxygen-containing compound feedstock and the catalyst to conduct the dehydration reaction to obtain a light olefins-rich hydrocarbon and a spent catalyst, transporting at least a part of the spent catalyst to the regeneration reaction to obtain a regenerated catalyst, and circulating at least a part of the regenerated catalyst to the dehydration reaction, wherein the reaction pressure P of the dehydration reaction is at least 0.35 MPa, preferably 0.4 MPa, 0.5 MPa, 0.6 MPa, 0.7 MPa, 0.8 MPa, 0.9 MPa, 1.0 MPa, 1.1 MPa, 1.2 MPa, 1.3 MPa, 1.4 MPa, 1.5 MPa, 1.6 MPa, 1.7 MPa, 1.8 MPa, 1.9 MPa or 2.0 MPa higher than the regeneration pressure of the regeneration reaction.

4. The process according to any of previous aspects, further comprising a step of separating the light olefins-rich hydrocarbon to obtain a $C_4^+$ hydrocarbon, and optionally further comprising the following steps:

continuously contacting the $C_4^+$ hydrocarbon and a further catalyst to conduct a further reaction to produce a further light olefins-rich hydrocarbon and a further spent catalyst, transporting at least a part of the further spent catalyst to the regeneration reaction to obtain a further regenerated catalyst, and circulating at least a part of the regenerated catalyst and/or at least a part of the further regenerated catalyst to the dehydration reaction and/or the further reaction.

5. The process according to any of previous aspects, wherein one or more reactors are used for the dehydration reaction and/or the further reaction, and each independently selected from a fluidized bed reactor, a dense bed reactor, a riser reactor, an ebullated bed reactor, a slurry bed reactor and a combination thereof, preferably selected from a riser reactor, more preferably each independently selected from an isodiametric riser reactor, a riser reactor with an equal linear velocity, a variable diameter riser reactor and a riser-dense bed hybrid reactor.

6. The process according to any of previous aspects, wherein the oxygen-containing compound feedstock is selected from at least one of alcohol, ether and ester, preferably selected from at least one of R1-O—R2, R1-OC(=O)O—R2, R1-C(=O)O—R2 and R1-C(=O)—R2 (wherein, R1 and R2 are identical or different each other, each independently selected from H and C1-6 branched or linear alkyl, preferably each independently selected from H and C1-4 branched or linear alkyl, with the proviso that at most one of R1 and R2 is hydrogen), more preferably selected from at least one of methanol, ethanol, dimethylether, diethylether, methylethyl-ether, methylene carbonate and methyl formate.

7. The process according to any of previous aspects, wherein the catalyst and the further catalyst are identical or different each other, each independently selected from at least one of zeolite catalysts, preferably each independently selected from at least one of aluminosilicophosphate zeolite catalysts and aluminosilicate molecular sieve catalysts.

8. The process according to any of previous aspects, wherein the reaction conditions of the regeneration reaction comprise: reaction temperature 450-850° C., preferably 550-700° C.; reaction pressure 0.1-0.5 MPa, preferably 0.15-0.3 MPa; oxygen-containing atmosphere, preferably air atmosphere or oxygen atmosphere.

9. The process according to any of previous aspects, wherein the spent catalyst and/or the further spent catalyst and/or the regenerated catalyst and/or the further regenerated catalyst are obtained by separation through a filter.

10. The process according to any of previous aspects, wherein the transporting and the circulating are performed via one or more (preferably one or two) catalyst hoppers (9).

11. The process according to any of previous aspects, further comprising a step of circulating at least a part of the spent catalyst and/or at least a part of the further spent catalyst to the dehydration reaction and/or the further reaction.

12. The process according to any of previous aspects, wherein the catalyst and/or the further catalyst have a total carbon content of 3-25 wt %, most preferably 6-15 wt %.

13. The process according to any of previous aspects, wherein with the proviso that the size and amount of the reactors for the dehydration reaction are kept the same, the process enables to increase the output of light olefins by 50%, preferably 100%, more preferably 150%, 200%, 500% or 790%, most preferably 1000% or higher.

14. The process according to any of previous aspects, further comprising a step of circulating an incompletely-reacted oxygen-containing compound feedstock to the dehydration reaction.

15. The process according to any of previous aspects, comprising the following steps:

continuously contacting the oxygen-containing compound feedstock and the catalyst in a riser-type reactor to conduct the dehydration reaction to produce a light olefins-rich hydrocarbon and a spent catalyst;

separating the olefins-rich hydrocarbon and the spent catalyst in a hydrocarbon-catalyst separation zone, introducing the separated olefins-rich hydrocarbon into a product separation-recovery system, stripping the spent catalyst through a stripping region of the riser-type reactor, withdrawing the spent catalyst from the riser-type reactor and transporting it to a spent catalyst receiver;

transporting the spent catalyst in the spent catalyst receiver directly to a regenerator via a catalyst hopper, or transporting it firstly to a spent catalyst feeding tank via a catalyst hopper and then to a regenerator, and regenerating the spent catalyst in an oxygen-containing atmosphere in the regenerator to obtain a regenerated catalyst;

transporting the regenerated catalyst directly to a catalyst hopper, or withdrawing the regenerated catalyst firstly from the regenerator and transporting it to the regenerated catalyst receiver, and then to a catalyst hopper;

transporting the regenerated catalyst in the catalyst hopper to the regenerated catalyst feeding tank, and then back to the riser-type reactor.

Technical Effects

Compared with the prior art, the process for producing light olefins according to the present invention have the following advantages.

The process for producing light olefins of the present invention, by means of increasing the reaction pressure and simultaneously and correspondingly increasing the WHSV of the oxygen-containing compound feedstock, with the proviso that the size and amount of the existing reactor or reaction plant is kept the same, enables to maintain the yield of light olefins at a level comparable to or even higher than that of the prior art, and remarkably increase the output of light olefins (e.g. by up to 790% or higher). Therefore, the process for producing light olefins according to the present invention is a process of increasing the output of light olefins, and can be applied to the reconstruction or upgrading of the existing light olefins production plant.

The process for producing light olefins according to the present invention, with the proviso of ensuring to achieve a predetermined output of light olefins, compared with the prior art, can remarkably reduce the size and amount of the reactor or reaction plant, and accordingly reduce the scale and investment cost of the whole light olefins production plant. Therefore, the process for producing light olefins according to the present invention is a new-generation process for producing light olefins with a high production capability, and can be applied to build a new-generation light olefins production plant with a smaller scale, a lower investment cost and a higher light olefin output than those of the existing light olefins production plant.

The process for producing light olefins according to the present invention maintains the operation of the regenerator under a lower pressure and the operation of the reactor under a higher pressure, and therefore reduces the overall complexity of the process for producing light olefins and the production plant.

The process for producing light olefins according to the present invention has a reaction pressure of the reactor remarkably higher than a regeneration pressure of the regenerator, and therefore the use of a pressure switch device (e.g. a lock hopper or a catalyst hopper) enables to implement the complete segregation of the hydrocarbon atmosphere of the reactor and the oxygen-containing atmosphere of the regenerator and the catalyst circulation, and accordingly ensure the overall safety of the production process and the production plant.

Other features and advantages of the present invention will be further discussed in the following part of Detailed Description of Invention.

BRIEF DESCRIPTION OF DRAWINGS

The drawings, which constitute a part of the specification, are used to provide a further understanding of the present invention, and serve to explain the present invention together with the following Detailed Description of Invention, but are not intended to limit the present invention. In the drawings.

Figure 1:
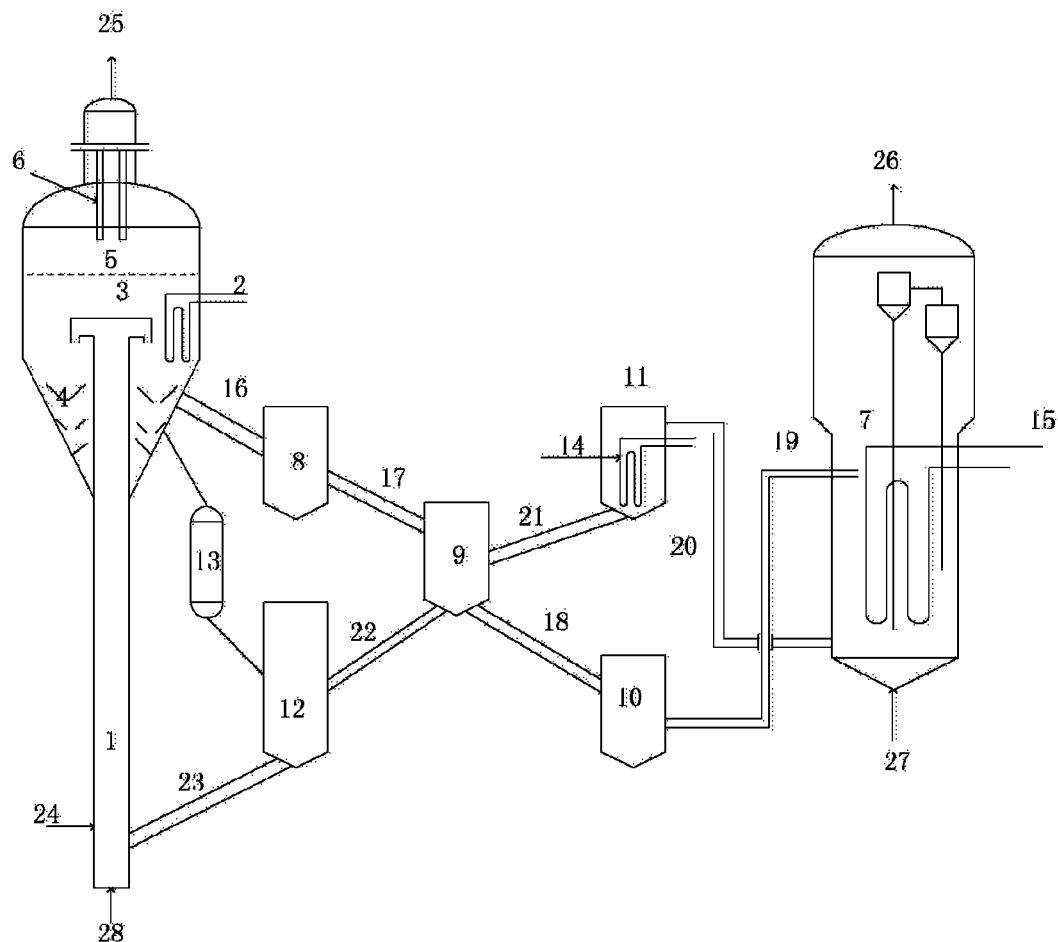
FIG. 1 is a flowchart of the process for producing light olefins from the oxygen-containing compound according to the first specific embodiment of the present invention

REFERENCE IN THE DRAWINGS 1 riser reactor; 2 internal heat remover; 3 dense bed reactor; 4 stripping region; 5 sedimentation zone; 6 filter; 7 regenerator; 8 spent catalyst receiver; 9 catalyst hopper; 10 spent catalyst feeding tank; 11 regenerated catalyst receiver; 12 regenerated catalyst feeding tank; 13 external heat remover; 14 internal heat remover; 15 internal heat remover; 16 pipeline; 17 pipeline; 18 pipeline; 19 pipeline; 20 pipeline; 21 pipeline; 22 pipeline; 23 pipeline; 24 feeding line; 25 reaction product line; 26 flue gas line; 27 pipeline; 28 pre-lifting line.

201 riser reactor; 202 internal riser and distributor; 203 dense bed reactor; 204 stripping region; 205 sedimentation zone; 206 filter; 207 regenerator; 208 spent catalyst receiver; 209 catalyst hopper; 210 regenerated catalyst receiver; 211 catalyst mixer; 212 regenerated catalyst feeding tank; 213 pipeline; 214 internal heat remover; 215 internal heat remover; 216 pipeline; 217 pipeline; 218 pipeline; 219 pre-lifting line; 220 quenching medium line; 221 pipeline; 222 pipeline; 223 pipeline; 224 feeding line; 225 reaction product line; 226 flue gas line; 227 pipeline; 301 riser reactor; 302 diameter-expanded riser; 303 dense bed reactor; 304 stripping region; 305 sedimentation zone; 306 filter; 307 regenerator; 308 spent catalyst receiver; 309 catalyst hopper; 310 spent catalyst feeding tank; 311 regenerated catalyst receiver; 312 regenerated catalyst feeding tank; 313 external heat remover; 314 internal heat remover; 315 internal heat remover; 316 pipeline; 317 pipeline; 318 pipeline; 319 pipeline; 320 pipeline; 321 pipeline; 322 pipeline; 323 pipeline; 324 feeding line; 325 reaction product line; 326 flue gas line; 327 pipeline; 328 pre-lifting line; 329 feeding line; 330 further riser-type reactor; 331 pipeline; 332 pipeline; 401 riser reactor; 402 internal riser and distribution plate; 403 dense bed reactor; 404 stripping region; 405 sedimentation zone; 406 filter; 407 regenerator; 408 spent catalyst receiver; 409 catalyst hopper; 410 regenerated catalyst receiver; 411 catalyst mixer; 412 regenerated catalyst feeding tank; 413 external heat remover; 414 internal heat remover; 415 internal heat remover; 416 pipeline; 417 pipeline; 418 pipeline; 419 pre-lifting line; 420 quenching medium line; 421 pipeline; 422 pipeline; 423 pipeline; 424 feeding line; 425 reaction product line; 426 flue gas line; 427 pipeline; 428 pre-lifting line; 429 feeding line; 430 pipeline; 431 first reaction zone; 432 second reaction zone; 433 necking and quick separator; 434 stripping region; 435 sedimentation zone; 436 filter; 437 pipeline; 438 pipeline; 501 riser reactor; 502 internal riser and quick separator; 503 dense bed reactor; 504 stripping region; 505 sedimentation zone; 506 filter; 507 regenerator; 508 spent catalyst receiver; 509 catalyst hopper; 510 spent catalyst feeding tank; 511 regenerated catalyst receiver; 512 catalyst feeding tank; 513 external heat remover; 514 internal heat remover; 515 internal heat remover; 516 pipeline; 517 pipeline; 518 pipeline; 519 pipeline; 520 pipeline; 521 pipeline; 522 pipeline; 523 pipeline; 524 feeding line; 525 reaction product line; 526 flue gas line; 527 pipeline; 528 quenching medium line; 529 external heat remover; 530 first reaction zone; 531 second reaction zone and necking; 532 pre-lifting line; 533 feeding line; 534 pipeline; 535 pipeline; 601 first reaction zone; 602 second reaction zone; 603 necking and quick separator; 604 stripping region; 605 sedimentation zone; 606 filter; 607 regenerator; 608 spent catalyst receiver; 609 catalyst hopper; 610 regenerated catalyst receiver; 611 catalyst mixer; 612 external heat remover; 613 external heat remover; 614 internal heat remover; 615 internal heat remover; 616 pipeline; 617 pipeline; 618 pipeline; 619 pre-lifting line; 620 flue gas line; 621 pipeline; 622 pipeline; 623 pipeline; 624 feeding line; 625 reaction product line; 626 pre-lifting line; 627 further riser-type reactor; 628 quick separator; 629 sedimentation zone; 630 stripping region; 631 filter; 632 reaction product line; 633 pipeline; 634 pipeline; 635 feeding line; 636 catalyst feeding tank; 637 pipeline; 701 fluidized bed reactor; 702 feeding line; 703 reaction product line; 704 flue gas line; 705 sedimentation zone; 706 filter; 707 regenerator; 708 spent catalyst receiver; 709 catalyst hopper; 710 spent catalyst feeding tank; 711 regenerated catalyst receiver; 712 regenerated catalyst feeding tank; 713 internal heat remover; 714 internal heat remover; 715 external heat remover; 716 pipeline; 717 pipeline; 718 pipeline; 719 pipeline; 720 pipeline; 721 pipeline; 722 pipeline; 723 pipeline; 724 main air.

DETAILED DESCRIPTION OF INVENTION

Hereinafter, the specific embodiments of the present invention will be discussed in details with reference to the drawings. It should be understood that the specific embodiments described herein are only intended to explain the present invention and the present invention is not limited thereto in any way.

In the context of the specification, the term "reactor" and "further reactor" refer to two reactors being independent each other. In the present invention, the term "$C_4^+$ hydrocarbon" refers to the hydrocarbon containing 4 or more carbon atoms.

In the context of the specification, the term "light olefins" refers to ethylene and propylene. In the context of the present specification, the term "yield of light olefins" refers to the once through yield of light olefins, the term "output of light olefins" refers to the once through output of light olefins per reactor in unit time, and the term "weight hourly space velocity" refers to the mass of the reactant passing through the unit mass of the catalyst in unit time.

Yield=the output of the product/the sum of the output of the hydrocarbon products except the oxygen-containing compound*100.

The hydrocarbon products except the oxygen-containing compound specifically include hydrogen and the hydrocarbons containing no oxygen and one or more carbon atoms.

According to the present invention, a process for producing light olefins is provided, wherein an oxygen-containing compound feedstock and a catalyst are continuously contacted to conduct a dehydration reaction to produce light olefins.

The process according to the present invention can comprise the following steps: continuously contacting an oxygen-containing compound feedstock and a catalyst to conduct the dehydration reaction to obtain a light olefins-rich hydrocarbon and a spent catalyst, transporting at least a part of the spent catalyst to the regeneration reaction to obtain a regenerated catalyst, and circulating at least a part of the regenerated catalyst to the dehydration reaction. Specifically speaking, the process can comprise the following steps: continuously contacting an oxygen-containing compound feedstock and a catalyst in a reactor (e.g. a riser-type reactor) to conduct the dehydration reaction to produce a light olefins-rich hydrocarbon and a spent catalyst; separating the olefins-rich hydrocarbon and the spent catalyst in a hydrocarbon-catalyst separation zone, introducing the separated olefins-rich hydrocarbon into a product separation-recovery system, stripping the spent catalyst through a stripping region of reactor, withdrawing the spent catalyst from the reactor and transporting it to a spent catalyst receiver; transporting the spent catalyst in the spent catalyst receiver directly to a regenerator via a catalyst hopper, or transporting it firstly to a spent catalyst feeding tank via a catalyst hopper and then to a regenerator, and regenerating the spent catalyst in an oxygen-containing atmosphere in the regenerator to obtain a regenerated catalyst; withdrawing the regenerated catalyst from the regenerator and transporting it to the regenerated catalyst receiver, and then to the regenerated catalyst feeding tank via a catalyst hopper, or transporting the regenerated catalyst directly to a catalyst hopper; and then transporting back to the reactor.

The regenerator according to the present invention can be any type of the regenerators known to those skilled in the art and conventionally used in the art, for example, a fluidized bed regenerator or an ebullated bed regenerator, but not limited thereto.

The process according to the present invention can also comprise the following steps: withdrawing a part of the spent catalyst from the reactor or the spent catalyst receiver; transporting the withdrawn spent catalyst directly to the reactor, or removing the heat from the withdrawn spent catalyst to cool it and then transporting the cooled catalyst to the reactor, or transporting the withdrawn spent catalyst to a catalyst mixer located at the lower part of the reactor to mix with the regenerated catalyst therein and then transporting the mixed catalyst to the reactor; wherein the withdrawn spent catalyst is in an amount sufficient to maintain the continuous operation of the catalyst in the reactor together with the regenerated catalyst that is transported to the regenerated catalyst feeding tank via a catalyst hopper. The process according to the present invention can also comprise the following steps: withdrawing a part of the spent catalyst from the reactor or the spent catalyst receiver; transporting the withdrawn spent catalyst directly to the regenerated catalyst feeding tank, or removing the heat from the withdrawn spent catalyst to cool it and then transporting the cooled catalyst to the regenerated catalyst feeding tank; after mixing with the regenerated catalyst, transporting the mixed catalyst to the reactor; wherein the withdrawn spent catalyst is in an amount sufficient to maintain the continuous operation of the catalyst in the reactor together with the regenerated catalyst that is transported to the regenerated catalyst feeding tank via a catalyst hopper.

According to the present invention, the oxygen-containing compound feedstock is well known to those skilled in the art, can be selected from at least one of alcohol, ether and ester, or can be other industrially or naturally sourced oxygen-containing compounds. The present invention has no specific limitation thereto. It is preferable for the oxygen-containing compound feedstock to be selected from at least one of R1-O—R2, R1-OC(=O)O—R2, R1-C(=O)O—R2 and R1-C(=O)—R2, wherein, R1 and R2 are identical or different each other, each independently selected from H and C1-6 branched or linear alkyl, preferably each independently selected from H and C1-4 branched or linear alkyl, with the proviso that at most one of R1 and R2 is hydrogen. It is more preferable for the oxygen-containing compound feedstock to be selected from at least one of methanol, ethanol, dimethylether, diethylether, methyl-ethyl-ether, methylene carbonate and methyl formate, in particular, methanol.

According to the present invention, a diluent is sometimes needed in the dehydration reaction. Water vapor is generally used as diluent, or hydrogen, methane, ethane, nitrogen, carbon monoxide or the like can be used as diluent. If used, the mole ratio of the oxygen-containing compound feedstock to the diluent is generally 40:1-0.4:1, preferably 11:1-0.7:1, more preferably 7:1-1.3:1.

According to the present invention, the used catalyst can be those well known to those skilled in the art. For example, the catalyst can be a zeolite catalyst. The zeolite can be an aluminosilicophosphate zeolite and/or an aluminosilicate zeolite. The aluminosilicophosphate zeolite can be selected from one or more of SAPO and SRM zeolites, and the aluminosilicate zeolite can be selected from one or more of ZSM and ZRP zeolites. In addition, the zeolite can be supported with one or more elements selected from alkaline earth metal, K, Mg, Ca, Ba, Zr, Ti, Co, Mo, Ni, Pt, Pd, La, Ce, Cu, Fe, B, Si, P, Sn, Pb, Ga, Cr, V, Sc, Ge, Mn, La, Al, Ni, and Fe.

The process according to the present invention can also comprise a step of separating the light olefins-rich hydrocarbon to obtain a $C_4^+$ hydrocarbon The process according to the present invention can optionally comprise the following steps: continuously contacting the $C_4^+$ hydrocarbon and a further catalyst to conduct a further reaction to produce a further light olefins-rich hydrocarbon and a further spent catalyst, transporting at least a part of the further spent catalyst to the regeneration reaction to obtain a further regenerated catalyst, and circulating at least a part of the regenerated catalyst and/or at least a part of the further regenerated catalyst to the dehydration reaction and/or the further reaction. For example, the process can comprise transporting the $C_4^+$ hydrocarbon obtained from the separation with the product separation-recovery system to the further reactor (e.g. a riser-type reactor) to conduct the further reaction.

According to the present invention, the further catalyst and the catalyst can be identical or different, and the further catalyst can be well known to those skilled in the art. For example, the further catalyst can be a zeolite catalyst. The zeolite can be an aluminosilicophosphate zeolite and/or an aluminosilicate zeolite. The aluminosilicophosphate zeolite can be selected from one or more of SAPO and SRM zeolites, and the aluminosilicate zeolite can be selected from one or more of ZSM and ZRP zeolites. In addition, the zeolite can be supported with one or more elements selected from alkaline earth metal, K, Mg, Ca, Ba, Zr, Ti, Co, Mo, Ni, Pt, Pd, La, Ce, Cu, Fe, B, Si, P, Sn, Pb, Ga, Cr, V, Sc, Ge, Mn, La, Al, Ni and Fe.

The process according to the present invention can also comprise the following steps: transporting the regenerated catalyst in the regenerated catalyst feeding tank to the further reactor to contact with the $C_4^+$ hydrocarbon and conduct the further reaction, and transporting the resulting further light olefins-rich hydrocarbon and the resulting further spent catalyst together to the hydrocarbon-catalyst separation zone of the reactor.

The process according to the present invention can also comprise the following steps: transporting the spent catalyst in the reactor to the further reactor to contact with the $C_4^+$ hydrocarbon and conduct the further reaction; separating the resulting further light olefins-rich hydrocarbon and the resulting further spent catalyst in the further reactor; and transporting the separated further light olefins-rich hydrocarbon to the product separation-recovery system, and transporting the separated further spent catalyst to the spent catalyst receiver.

The process according to the present invention can also comprise the following steps: transporting the spent catalyst in the reactor to the further reactor to contact with the $C_4^+$ hydrocarbon and conduct the further reaction, and transporting the resulting further light olefins-rich hydrocarbon and the resulting further spent catalyst together to the hydrocarbon-catalyst separation zone of the reactor.

The process according to the present invention can also comprise the following steps: transporting the regenerated catalyst in the regenerator directly to the further reactor to contact with the $C_4^+$ hydrocarbon and conduct the further reaction to obtain a further light olefins-rich hydrocarbon and a further spent catalyst; separating the further light olefins-rich hydrocarbon and the further spent catalyst in the further reactor; transporting the separated further light olefins-rich hydrocarbon to the product separation-recovery system; and transporting the further spent catalyst directly to the regenerator to conduct the regeneration.

According to the present invention, the number of the reactor and/or the further reactor can be one or more, and the present invention has no specific limitation thereto. In addition, the reactor and/or the further reactor are identical or different each other, and each independently selected from a fluidized bed reactor, a dense bed reactor, a riser reactor, an ebullated bed reactor, a slurry bed reactor and a combination thereof. It is preferable that the reactor and/or the further reactor are identical or different each other, and each independently selected from a riser reactor, more preferably each independently selected from an isodiametric riser reactor, a riser reactor with an equal linear velocity, a variable diameter riser reactor and a riser-dense bed hybrid reactor. In addition, in the vertical direction from the bottom to the top, the riser-type reactor can be also provided with a pre-lifting region, a riser, a quenching medium line, a diameter-expanded riser, a necking, a quick separator, a stripping region, a dense-phase region, a sedimentation zone, a catalyst mixer, and a filter, which are industrially common devices, so that the reactor can be continuously operated; wherein the sedimentation zone, the filter and the like can constitute the hydrocarbon-catalyst separation zone, and the hydrocarbon-catalyst separation zone can also comprise other devices useful for the separation of the spent catalyst and the hydrocarbon. The present invention has no limitation thereto. According to the present invention, the dense bed part of the riser-type reactor can form no dense bed, i.e. "zero-bed" operating mode.

Since the process for producing olefins from the oxygen-containing compound feedstock is an exothermic reaction, the reactor according to the present invention can be provided with one or more quenching medium lines to control the reaction temperature. According to a specific embodiment of the present invention, one or more quenching medium lines can be provided at the mid-downstream of the reactor (relative to the reactant direction) so as to inject a quenching medium to the reactor. The shock chilling medium can be a quenching agent or a cooled catalyst. The quenching agent can be an un-preheated oxygen-containing compound feedstock and/or water.

According to the present invention, in general, the reaction temperature of the dehydration reaction is 200-700° C., preferably 250-600° C. In particular, in order to achieve the present inventive object of increasing the production of light olefins, the reaction pressure P of the dehydration reaction is 0.5-10 MPa, preferably 0.75-3.5 MPa, more preferably 0.8-3 MPa, most preferably 1-2 MPa. In addition, the weight hourly space velocity H of the dehydration reaction is generally 7-250 $h^{-1}$, preferably 8-150 $h^{-1}$, more preferably 10-100 $h^{-1}$, more preferably 15-80 $h^{-1}$, most preferably 15-50 $h^{-1}$.

According to a particularly preferable embodiment of the present invention, in the dehydration reaction (in other words, if intending to remarkably increase the output of light olefins upon doing a modification based on an existing reactor or reaction plant), H and P satisfy a mathematical function of H=f(P), which is a strictly increasing function. Among others, P (unit: MPa) is in the interval [0.55, 10.0], preferably in the interval [0.75, 3.5], more preferably in the interval [0.8, 3.0], more preferably in the interval [1.0, 2.0], and H (unit: $h^{-1}$) is in the interval [7, 250], preferably in the interval [8, 150], more preferably in the interval [10, 100], more preferably in the interval [15, 80], most preferably in the interval [15, 50]. According to this strictly increasing function, when the reaction pressure P of the dehydration reaction is increased in the specific numeric interval as defined in the present invention, the weight hourly space velocity H of the dehydration reaction should be correspondingly increased in the specific numeric interval as defined in the present invention. The present invention has no limitation to the increasing manner and the increasing amplitude of the reaction pressure P and the weight hourly space velocity H, as long as based on the normal judgement of those skilled in the art, the numerical values are indeed increased respectively; and it is not allowed to remain the numerical values unchanged or decrease the numerical values. According to one specific embodiment of the present invention, it is preferable that the reaction pressure P and the weight hourly space velocity H are increased in proportion or in the same or different amplitude, sometimes in the same scale or synchronously, until the expected amplitude of increasing the production of light olefins is accomplished. In some cases, when the reaction pressure P arrives at the upper limit (e.g. 3 MPa) of a certain numeric interval as defined previously in the present invention, it is generally preferable that the weight hourly space velocity H arrives at the upper limit (e.g. 50 $h^{-1}$) of a certain numeric interval as defined previously in the present invention too, but not limited thereto.

It should be particularly noted that, when any one or both of the reaction pressure P and the weight hourly space velocity H are not in the numeric range or the numeric interval as previously defined herein, even increasing the reaction pressure P and simultaneously and correspondingly increasing the weight hourly space velocity H cannot obtain the effect of remarkably increasing the production of light olefins of the present invention, as shown in the Example. This is totally unexpected by those skilled in the art.

According to the present invention, the reaction conditions of the further reaction comprise: reaction temperature 200-700° C., preferably 300-600° C.; reaction pressure 0.1-6 MPa, preferably 0.8-2 MPa. The process according to the present invention can also comprise: controlling the ratio of the reaction pressure P of the reactor to the regeneration pressure of the regenerator to be 3-100:1. More specifically speaking, according to the present invention, the reaction pressure P of the dehydration reaction is at least 0.35 MPa, preferably 0.4 MPa, 0.5 MPa, 0.6 MPa, 0.7 MPa, 0.8 MPa, 0.9 MPa, 1.0 MPa, 1.1 MPa, 1.2 MPa, 1.3 MPa, 1.4 MPa, 1.5 MPa, 1.6 MPa, 1.7 MPa, 1.8 MPa, 1.9 MPa or 2.0 MPa higher than the regeneration pressure of the regeneration reaction. Alternatively according to the present invention, the reaction pressure P of the dehydration reaction is at most 5 MPa, preferably 4 MPa, 3.5 MPa, 3.3 MPa, 3 MPa, 2.5 MPa, 2.3 MPa, 2 MPa, 1.5 MPa, 1.3 MPa or 1 MPa higher than the regeneration pressure of the regeneration reaction.

According to the present invention, since the production of light olefins from the oxygen-containing compound feedstock and the regenerate of the spent catalyst are the exothermic reactions, one or more internal heat removers can be installed in the reactor, the regenerator, the regenerated catalyst feeding tank or the regenerated catalyst receiver. The internal heat remover can be in form of coil pipe, elbow pipe and the like. The heat in the reactor can be removed by the liquid such as water or carbon tetrachloride flowing in the internal heat remover. Other internal heat remover commonly used in the industry can be also applied in the present invention.

The present inventors have found that contacting the oxygen-containing compound feedstock with a certainly-coked catalyst can be favorable for the reaction to proceed quickly. This is because, on one hand, the coke deposited in the catalyst continuously reacts as active center with the oxygen-containing compound feedstock to introduce the alkyl groups; on the other hand, the coke deposited in the catalyst is continuously dealkylated to form the light olefins such as propylene and ethylene. This is the so-called "hydrocarbon pool" reaction. Accordingly, the process according to the present invention can also comprise circulating at least a part of the spent catalyst and/or at least a part of the further spent catalyst to the dehydration reaction or the reactor.

According to a specific embodiment of the present invention, a part of the spent catalyst can be withdrawn from the reactor or the spent catalyst receiver, the withdrawn spent catalyst is transported, directly or via heat removal to reduce the temperature, back to the reactor, or transported to the catalyst mixer located at the lower part of the reactor, in which the spent catalyst and the regenerated catalyst are mixed, and then the resulting mixed catalyst is transported back to the reactor for reaction.

According to another specific embodiment of the present invention, a part of the spent catalyst can be withdrawn from the reactor or the spent catalyst receiver, the withdrawn spent catalyst is transported, directly or via heat removal to reduce the temperature, to regenerated catalyst feeding tank, in which the spent catalyst and the regenerated catalyst are mixed, and then the resulting mixed catalyst is transported back to the reactor; wherein the withdrawn spent catalyst is in an amount sufficient to maintain the continuous operation of the catalyst in the reactor together with the regenerated catalyst that is present in the regenerated catalyst feeding tank and transported via a catalyst hopper.

According to the present invention, a part of the spent catalyst withdrawn from the reactor or the spent catalyst receiver can be transported via the external heat remover, in which the heat is removed so as to reduce the temperature. Said external heat remover can be well known to those skilled in the art, and the heat removal device such as coil pipe and elbow pipe can be installed in the external heat remover to reduce the temperature of the spent catalyst flowing therethrough.

According to the present invention, the catalyst mixer can be connected to the reactor, preferably in a vertical manner, for mixing one or more the hot regenerated catalyst, the heat-removed regenerated catalyst, and the spent catalyst that are transported to the reactor. The catalyst mixer has a temperature of 200-600° C., preferably 300-500° C., and a pressure of 0.5-10 MPa.

According to the present invention, the total carbon content of the catalyst(s) transported to the reactor (the feeding zone) and/or the further reactor (the feeding zone) can be 3-25 wt %, preferably 6-15 wt %. Here, the catalyst transported to the reactor or the further reactor can be from the regenerated catalyst feeding tank, or can be from the spent catalyst receiver and/or the reactor, wherein the catalyst from the regenerated catalyst feeding tank can be a regenerated catalyst, or a mixed catalyst of the regenerated catalyst and the spent catalyst.

According to the present invention, it can be understood by those skilled in the art that the light olefins-rich hydrocarbon can be separated by the product separation-recovery system to produce a fraction of $C_4^+$ hydrocarbon. In order to increase the output of the light olefins, the $C_4^+$ hydrocarbon can be transported to the further reactor to conduct the further reaction for cracking the $C_4^+$ hydrocarbon into light olefins.

According to a specific embodiment of the present invention, the regenerated catalyst in the regenerated catalyst feeding tank can be transported to the further reactor to contact with the $C_4^+$ hydrocarbon and conduct the further reaction, and the resulting further light olefins-rich hydrocarbon and the resulting further spent catalyst are transported together to the hydrocarbon-catalyst separation zone of the reactor; wherein the further light olefins-rich hydrocarbon and the further spent catalyst that are transported to the hydrocarbon-catalyst separation zone of the reactor can be mixed with the light olefins-rich hydrocarbon and the spent catalyst that are produced in the reactor, and the resulting mixture is then subjected to the separation.

According to a further specific embodiment of the present invention, the spent catalyst in the reactor can be transported to the further reactor to contact with the $C_4^+$ hydrocarbon and conduct the further reaction, the resulting further light olefins-rich hydrocarbon and the resulting further spent catalyst can be separated in the further reactor, the separated further light olefins-rich hydrocarbon is transported to the product separation-recovery system, and the separated further spent catalyst is transported to the spent catalyst receiver.

According to a further specific embodiment of the present invention, the spent catalyst that has been stripped in the stripping region of the reactor can be transported to the further reactor to contact with the $C_4^+$ hydrocarbon and conduct the further reaction, the resulting further light olefins-rich hydrocarbon and the resulting further spent catalyst are transported together to the hydrocarbon-catalyst separation zone of the reactor; wherein the further light olefins-rich hydrocarbon and the further spent catalyst that are transported back to the reactor can be mixed with the light olefins-rich hydrocarbon and the spent catalyst that are produced in the reactor, and the resulting mixture is then subjected to the separation.

According to a more further specific embodiment of the present invention, the regenerated catalyst in the regenerator can be directly transported to the further reactor to contact with the $C_4^+$ hydrocarbon and conduct the further reaction to produce a further light olefins-rich hydrocarbon and a further spent catalyst is separated in the further reactor; the further light olefins-rich hydrocarbon and the further spent catalyst are separated in the further reactor, the separated further light olefins-rich hydrocarbon can be transported to the product separation-recovery system, and the separated further spent catalyst can be directly transported to the regenerator for regeneration.

According to the present invention, the reaction conditions that are well known to those skilled in the art and can produce light olefins can be applied to the dehydration reaction for producing olefin in the reactor and the further reaction in the further reactor, and the substantially same or different reaction conditions can be applied to the above two reactions. Since the reaction feedstock in the further reactor and the reaction feedstock in the reactor are not completely identical, therefore it is preferable that depending on the feedstock in the further reactor, the reaction conditions, which are different from those of the reactor, are applied to the further reaction, which can be understood by those skilled in the art, wherein the further reaction can mainly comprise the cracking reaction of $C_4^+$ hydrocarbon. It is preferable that the reaction conditions in two reactors can be selected, for example, in the following ranges: the reaction temperature can be 200-700° C., preferably 250-600° C.; the reaction pressure can be 0.5-10 MPa, preferably 1-3.5 MPa.

In order to separate the (further) light olefins-rich hydrocarbon and the (further) spent catalyst produced after the reaction in the reactor or the further reactor, or to separate the regenerated catalyst and the flue gas produced after the regeneration in the regenerator, the conventional cyclone separator can be used, which is well known to those skilled in the art, and will not be discussed in detail.

According to a preferred specific embodiment of the present invention, the light olefins-rich hydrocarbon and the spent catalyst can be separated with a filter. In addition, the further light olefins-rich hydrocarbon and the further spent catalyst can be also separated with a filter. Moreover, the (further) regenerated catalyst and the flue gas can be also separated with a filter. The use of the filter to separate the catalyst can effectively remove the catalyst powder and dust entrained in the hydrocarbon or the flue gas. Compared with the cyclone separator conventionally used in the prior art, the use of the filter can maximally reduce the natural loss of the catalyst in the production. This is one of remarkable dominances of the present invention.

According to the present invention, the filter can be prepared with a porous material, for example, selected from metal sintered porous material and/or ceramic porous material. The filter has a filter fineness for 2 μm particle of as high as 99.9%, preferably a filter fineness for 1.2 μm particle of as high as 99.9%. In addition, the filter can be purged with a purge gas to clean off the filter cake. Herein, the purge gas can be selected from one or more of a hydrocarbon-containing gas, dry gas, nitrogen, and water vapor.

The process according to the present invention can also comprise circulating an incompletely-reacted oxygen-containing compound feedstock (including various oxygen-containing compounds newly formed in the dehydration reaction, especially dimethyl ether) to the step of the dehydration reaction to accomplish the full utilization of the reaction feedstock.

According to the present invention, transporting at least a part of the spent catalyst and/or at least a part of the further spent catalyst to the regeneration reaction and/or transporting at least a part of the regenerated catalyst and/or at least a part of the further regenerated catalyst to the dehydration reaction and/or the further reaction can be conveniently accomplished by means of one or more (preferably one or two) catalyst hopper. Herein, the catalyst hopper is sometimes also known as the lock hopper. In the context of the present specification, in particular in the drawings and the Example, the catalyst hopper is taken as an example to explain the technology idea of the present invention and various specific embodiments, but the present invention is not limited thereto.

According to the present invention, the catalyst hopper can safely and effectively transport the catalyst from a higher pressure hydrocarbon environment of the reactor to a lower pressure oxygen environment of the regenerator, and from a lower pressure oxygen environment of the regenerator to a higher pressure hydrocarbon environment of the reactor.

That is to say, on one hand, the use of the catalyst hopper can segregate the hydrocarbon atmosphere of the reactor from the regenerative oxygen-containing atmosphere of the regenerator, ensuring the safety of the process of the present invention; on the other hand, can flexibly adjust and control the operation pressure of the reactor and the regenerator, in particular in case of not increasing the operation pressure of the regenerator, can increase the operation pressure of the reactor and thereby increase the plant's throughput.

For example, the step of transporting a catalyst from a reactor (higher pressure hydrocarbon environment) to a regenerator (lower pressure oxygen environment) through a catalyst hopper can comprise: 1. purging the evacuated catalyst hopper with a hot nitrogen to drive the residual oxygen to the regenerator; 2. purging the catalyst hopper with dry gas to drive out the nitrogen; 3. pressurizing the evacuated catalyst hopper with dry gas; 4. filling the evacuated catalyst hopper with the spent catalyst transported from the spent catalyst receiver; 5. depressurizing the filled catalyst hopper by venting the dry gas in the pressurized catalyst hopper; 6. purging the filled catalyst hopper with hot nitrogen to drive out the dry gas; 7. discharging the spent catalyst from the filled catalyst hopper to the spent catalyst feeding tank. For example, the step of circulating a catalyst from a regenerator (lower pressure oxygen environment) to a reactor (higher pressure hydrocarbon environment) through a catalyst hopper can comprise: 1. purging the regenerated catalyst-filled catalyst hopper with hot nitrogen to drive the oxygen to the regenerator; 2. purging the catalyst hopper with dry gas to drive out the nitrogen; 3. pressurizing the filled catalyst hopper with dry gas; 4. discharging the regenerated catalyst from the filled catalyst hopper to the regenerated catalyst feeding tank; 5. depressurizing the evacuated catalyst hopper by venting the dry gas in the pressurized catalyst hopper; 6. purging the evacuated catalyst hopper with hot nitrogen to drive out the dry gas; 7. filling the evacuated catalyst hopper with the regenerated catalyst transported from the regenerated catalyst receiver.

Since the catalyst is transported with the catalyst hopper in batch, according to the present invention, the function of the regenerated catalyst feeding tank and the spent catalyst circulating line is to transport the catalyst to the reactor in a more continuous manner. However, the present inventors have found that transporting the spent catalyst to the regenerator and transporting the regenerated catalyst from the regenerator can be done in batch. Upon transporting the spent catalyst from the catalyst hopper to the regenerator or upon transporting the regenerated catalyst from the regenerator to the catalyst hopper, the transport can be accomplished by means of the gravity between the regenerator and the catalyst hopper or the pressure difference between the pipelines without installing the spent catalyst feeding tank or the regenerated catalyst receiver.

According to the present invention, in case that the further reactor and the reactor are communicated with each other, those skilled in the art can understand that the pressures in two reactors can be identical, that is to say, if necessary, the catalyst hopper can also accomplish the transport and circulating of the catalyst in the further reactor.

According to the present invention, the regeneration reaction conditions are well known to those skilled in the art, for example, the reaction conditions of the regeneration reaction comprise: reaction temperature 450-850° C., preferably 550-700° C.; reaction pressure 0.1-0.5 MPa, preferably 0.15-0.3 MPa, for example normal pressure; oxygen-containing atmosphere. The oxygen-containing atmosphere can be air, a nitrogen-diluted air, an oxygen-rich gas as fluidizing medium.

According to the present invention, with the proviso that the size and amount of the reactor for the dehydrogenation reaction are kept the same; in other words, upon doing a modification based on an existing reactor or reaction plant, increasing the reaction pressure and WHSV of the reactor in the specific ranges as defined according to the present invention can remarkably increase the throughput of the oxygen-containing compound feedstock of the reactor and accordingly increase the output of the light olefins. In this case, the output of light olefins can be increased by up to 50%, preferably 100%, more preferably 150%, 200%, 500% or 790%, most preferably even up to 1000% or higher.

It should be emphasized that, according to the present invention, on the basis that the yield of light olefins is kept at a level substantially identical to or slightly higher than that of the prior art, the object of increasing the output of light olefins is accomplished by increasing the throughput of the oxygen-containing compound feedstock of the reactor or reaction plant. Therefore, the amplitude of increasing of the output of the light olefins according to the present invention is remarkably higher, compared with the achievement of increasing the output of light olefins by simply increasing the throughput of the oxygen-containing compound feedstock of the reactor or reaction plant at the expense of compromising the yield of light olefins (for example, the reduction amplitude >20%). According to the present invention, the yield of light olefins can be maintained at a level comparable to or even higher than that of the prior art, for example, generally 60%-95% or 78%-95%.

From another viewpoint, with the proviso that a predetermined output of light olefins is achieved, compared to the prior art, the production of light olefins according to the process of the present invention as previously defined can remarkably reduce the size and amount of the reactor or reaction plant, and therefore reduce the scale and investment cost of the whole light olefins production plant. The specific embodiments of the present invention will be further described with reference to the drawings, but the present invention is not limited thereto. For convenience of describing the present invention, a riser-type reactor is taken as an example of the reactor, but the present invention is not limited thereto.

First Specific Embodiment

FIG. 1 is a flowchart of the process for producing light olefins from the oxygen-containing compound feedstock according to the first specific embodiment of the present invention.

As shown in FIG. 1, the oxygen-containing compound feedstock from the feeding line 24 is transported to the riser reactor 1 of the riser-type reactor, and is contacted with the catalyst from the pipeline 23 and lifted by means of the pre-lifting line 28 to conduct the dehydration reaction to produce olefins. After the reaction, the resulting hydrocarbon product enters the dense bed reactor 3. An excessive heat is removed from the dense bed reactor 3 with the internal heat remover 2. The hydrocarbon product is further reacted in the dense bed reactor 3. The resulting light olefins-rich hydrocarbon and the spent catalyst are transported to the sedimentation zone 5. After sedimentation, the spent catalyst returns to the dense bed reactor 3. The light olefins-rich hydrocarbon and the entrapped spent catalyst fine powder are filtered with the filter 6. The light olefins-rich hydrocarbon is transported to a product separation-recovery system (not shown) via the pipeline 2. After filtering, the spent catalyst fine powder settles and returns to the dense bed reactor 3. The spent catalyst is stripped in the stripping region 4. After stripping, a part of the spent catalyst is transported to the spent catalyst receiver 8 via the pipeline 16, and the other part of the spent catalyst is subjected to a heat-removal with the external heat remover 13 and transported to the regenerated catalyst feeding tank 12.

The spent catalyst from the spent catalyst receiver 8 is transported to the catalyst hopper 9 via the pipeline 17, transported to the spent catalyst feeding tank 10 via the pipeline 18 after the pressure release, and then transported to the regenerator 7 via the pipeline 19. The spent catalyst is counter-current contacted with the main air from the pipeline 27 and subjected to regeneration by coke-burning. The excessive heat is removed with the internal heat remover 15 (the removed heat can be controlled with the amount of the heat-removing stream and the depth by which the internal heat remover 15 is embedded into the dense bed layer). The flue gas is transported via the pipeline 26 to the subsequent energy recovery and purification system (not shown). The regenerated catalyst is transported to the regenerated catalyst receiver 11 via the pipeline 20. The excessive heat of the regenerated catalyst is removed with the internal heat remover 14. After the heat removal, the regenerated catalyst is transported to the catalyst hopper 9 via the pipeline 21. After increasing the pressure, the regenerated catalyst is transported to the regenerated catalyst feeding tank 12 via the pipeline 22 and mixed with the spent catalyst from the heat remover 13. The mixed catalyst is transported to the pre-lifting region of the riser reactor 1 via the pipeline 23.

Second Specific Embodiment

Figure 2:
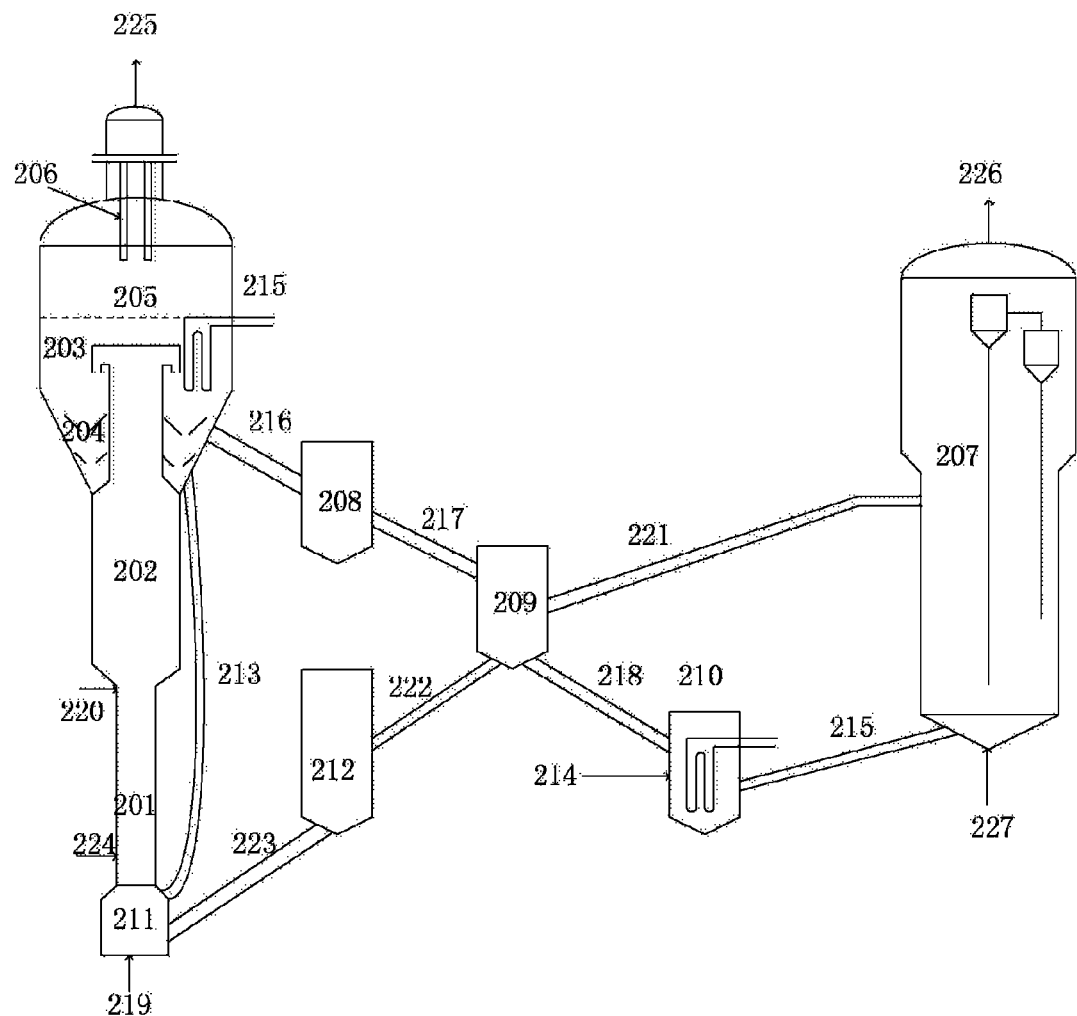
FIG. 2 is a flowchart of the process for producing light olefins from the oxygen-containing compound according to the second specific embodiment of the present invention

FIG. 2 is a flowchart of the process for producing light olefins from the oxygen-containing compound feedstock according to the second specific embodiment of the present invention.

As shown in FIG. 2, the catalyst from the pipeline 223 and the spent catalyst from the pipeline 213 are mixed in the catalyst mixer 211. The mixed catalyst is lifted with the pre-lifting gas from the pre-lifting line 219 and transported to the riser reactor 201 of the riser-type reactor. The oxygen-containing compound feedstock is transported to the riser reactor 201 via the feeding line 224, and contacted with the catalyst from the mixer 211 to conduct the dehydration reaction to produce olefins. After the reaction, the resulting hydrocarbon product is further reacted in the internal riser and distributor 202, and then transported to the dense bed reactor 203. The quenching medium from the quenching medium line 220 is transported to the riser reactor 201 to control the reaction temperature. The unconverted feedstock is further contacted with the catalyst and reacted in the dense bed reactor 203. The excessive reaction heat is withdrawn with the internal heat remover 215. The resulting light olefins-rich hydrocarbon and the spent catalyst are transported to the sedimentation zone 205. After sedimentation, the spent catalyst returns to the dense bed reactor 203. The light olefins-rich hydrocarbon and the entrapped spent catalyst fine powder are filtered with the filter 206. The light olefins-rich hydrocarbon is transported to a product separation-recovery system (not shown) via the pipeline 225. After filtering, the spent catalyst fine powder settles and returns to the dense bed reactor 203. The spent catalyst is stripped in the stripping region 204. After stripping, a part of the spent catalyst is transported back to the catalyst mixer 211 via the pipeline 213, and another part of the spent catalyst is transported to the spent catalyst receiver 208 via the pipeline 216.

The spent catalyst from the spent catalyst receiver 208 is transported to the catalyst hopper 209 via the pipeline 217, and transported to the regenerator 207 via the pipeline 221 after the pressure release. The spent catalyst is counter-current contacted with the main air from the pipeline 227 and subjected to regeneration by coke-burning. The flue gas is transported via the pipeline 226 to the subsequent energy recovery and purification system (not shown). The regenerated catalyst is transported to the regenerated catalyst receiver 210 via the pipeline 215. The excessive heat of the regenerated catalyst is removed with the internal heat remover 214. After the heat removal, the regenerated catalyst is transported to the catalyst hopper 209 via the pipeline 218. After increasing the pressure, the regenerated catalyst is transported to the regenerated catalyst feeding tank 212 via the pipeline 222 and transported to the catalyst mixer 211 via the pipeline 223.

Third Specific Embodiment

Figure 3:
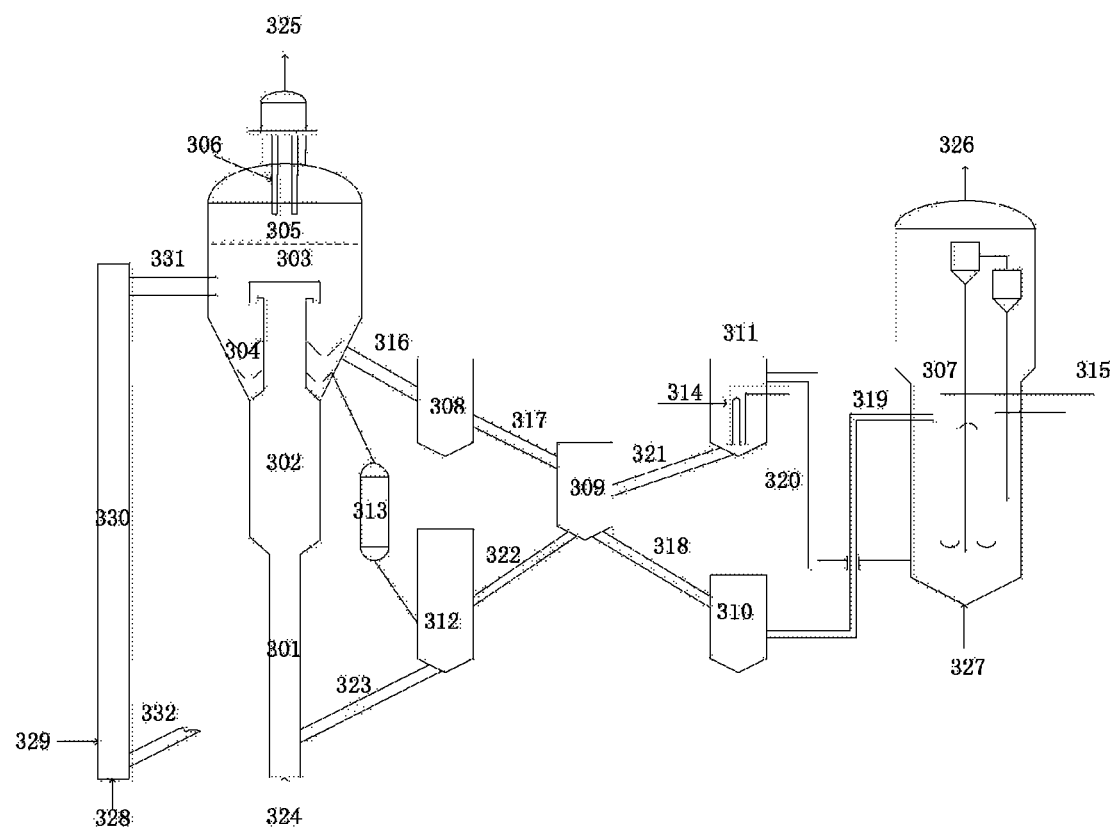
FIG. 3 is a flowchart of the process for producing light olefins from the oxygen-containing compound according to the third specific embodiment of the present invention

FIG. 3 is a flowchart of the process for producing light olefins from the oxygen-containing compound feedstock according to the third specific embodiment of the present invention.

As shown in FIG. 3, the oxygen-containing compound feedstock is transported to the riser reactor 301 of the riser-type reactor via the feeding line 324, and contacted with the catalyst from the pipeline 323 to conduct the dehydration reaction to produce olefins. After the reaction, the resulting hydrocarbon product is further reacted in the diameter-expanded riser 302, and then further reacted in the dense bed reactor 303. The resulting light olefins-rich hydrocarbon and the spent catalyst are transported to the sedimentation zone 305. After sedimentation, the spent catalyst returns to the dense bed reactor. The light olefins-rich hydrocarbon and the entrapped spent catalyst fine powder are filtered with the filter 306. The light olefins-rich hydrocarbon is transported to a product separation-recovery system (not shown) via the pipeline 325. After filtering, the spent catalyst fine powder settles and returns to the stripping region 304 of the dense bed reactor 203. After stripping, a part of the spent catalyst is transported back to the spent catalyst receiver 308 via the pipeline 316, and another part of the spent catalyst is transported to the external heat remover 313, and transported to the regenerated catalyst feeding tank 312 after heat removal.

The spent catalyst from the spent catalyst receiver 308 is transported to the catalyst hopper 309 via the pipeline 317, transported to the spent catalyst feeding tank 310 via the pipeline 318 after the pressure release, and then transported to the regenerator 307 via the pipeline 319. The spent catalyst is counter-current contacted with the main air from the pipeline 327 and subjected to regeneration by coke-burning. The excessive heat is removed with the internal heat remover 315 (the removed heat can be controlled with the amount of the heat-removing stream and the depth by which the internal heat remover 315 is embedded into the dense bed layer). The flue gas is transported via the pipeline 326 to the subsequent energy recovery and purification system (not shown). The regenerated catalyst is transported to the regenerated catalyst receiver 311 via the pipeline 320. The excessive heat of the regenerated catalyst is removed with the internal heat remover 314. After the heat removal, the regenerated catalyst is transported to the catalyst hopper 309 via the pipeline 321. After increasing the pressure, the regenerated catalyst is transported to the regenerated catalyst feeding tank 312 via the pipeline 322 and mixed with the spent catalyst from the external heat remover 313. The mixed catalyst is transported to the riser reactor 301 and to the further riser-type reactor 330 via the pipelines 323 and 332.

The catalyst from the pipeline 332 is transported to the pre-lifting region of the further riser-type reactor 330, and further transported to the further riser-type reactor 330 by lifting with the pre-lifting media from the pre-lifting line 328. The $C_4^+$ hydrocarbon obtained from the separation of the product separation-recovery system is transported to the further riser-type reactor 330 via the feedstock feeding line 329 and contacted with the catalyst to conduct the further reaction. The resulting light olefins-rich hydrocarbon is transported to the dense bed-fluidized bed 303 via the pipeline 331.

Fourth Specific Embodiment

Figure 4:
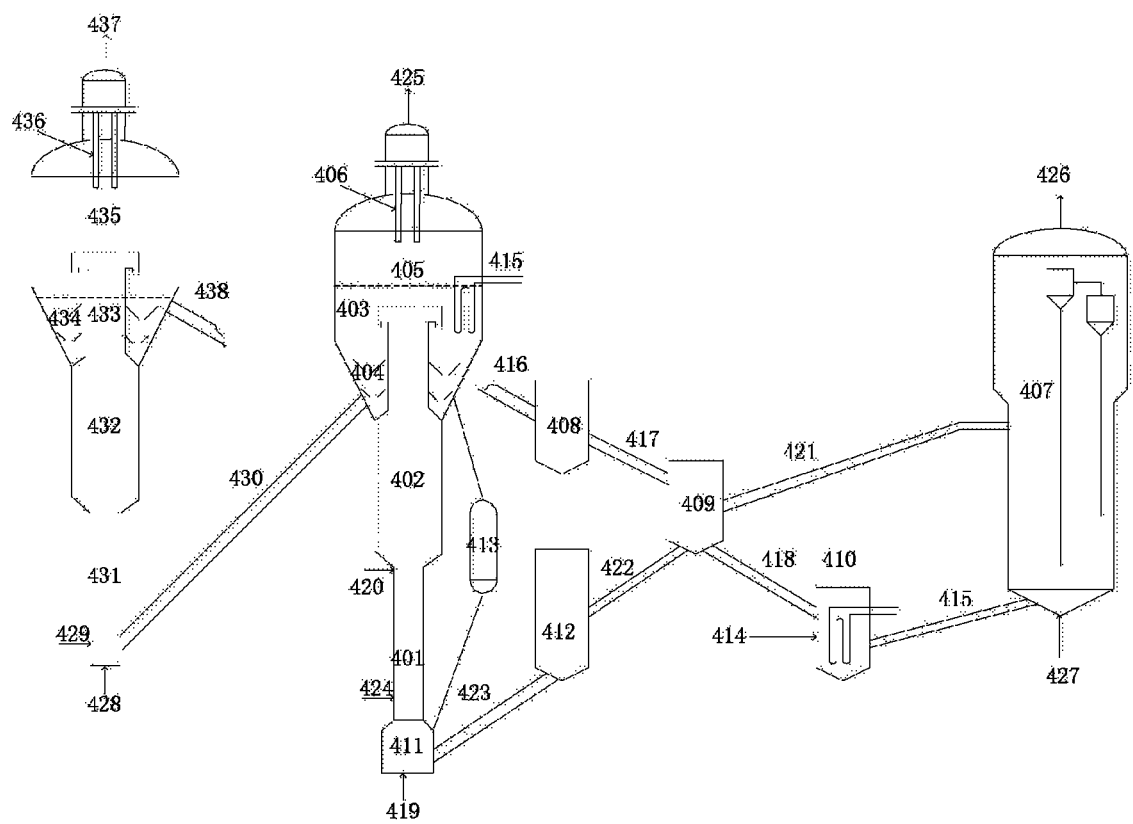
FIG. 4 is a flowchart of the process for producing light olefins from the oxygen-containing compound according to the fourth specific embodiment of the present invention

FIG. 4 is a flowchart of the process for producing light olefins from the oxygen-containing compound feedstock according to the fourth specific embodiment of the present invention.

As shown in FIG. 4, the catalyst from the pipeline 423 and the spent catalyst from the external heat remover 413 are mixed in the catalyst mixer 411. The mixed catalyst is lifted with the pre-lifting gas from the pre-lifting line 419 and transported to the riser reactor 401 of the riser-type reactor. The oxygen-containing compound feedstock is transported to the riser reactor 401 via the feeding line 424, and contacted with the catalyst from the catalyst mixer 411 to conduct the dehydration reaction to produce olefins. After the reaction, the resulting hydrocarbon product and the catalyst are transported to the dense bed reactor 403 via the internal riser and distribution plate 402. The quenching medium from the quenching medium line 420 is transported to the riser reactor 401 to control the reaction temperature. The unconverted feedstock is further contacted with the catalyst and reacted in the dense bed reactor 403. The excessive reaction heat is withdrawn with the internal heat remover 415. The resulting light olefins-rich hydrocarbon and the spent catalyst are transported to the sedimentation zone 205. After sedimentation, the spent catalyst is transported to the stripping region 404. The light olefins-rich hydrocarbon and the entrapped spent catalyst fine powder are filtered with the filter 406. After filtering, the light olefins-rich hydrocarbon is transported to a product separation-recovery system (not shown) via the pipeline 425, and the spent catalyst fine powder settles and returns to the dense bed reactor 403. The spent catalyst is stripped in the stripping region 404. After stripping, a part of the spent catalyst is transported back to the catalyst mixer 411 via the internal heat remover 413, and another part of the spent catalyst is transported to the first reaction zone 431 of the further riser-type reactor via the pipeline 430. The $C_4^+$ hydrocarbon obtained from the separation of the product separation-recovery system is transported to the first reaction zone 431 of the further riser-type reactor via the pipeline 429 and contacted with the catalyst from the pipeline 430 to conduct the further reaction. The resulting light olefins-rich hydrocarbon and the resulting catalyst are transported to the second reaction zone 432 to continue the reaction, and then to the sedimentation zone 435 via the quick separator 433 at the necking. The light olefins-rich hydrocarbon and the entrapped spent catalyst fine powder are filtered with the filter 436. After filtering, the light olefins-rich hydrocarbon is transported to a product separation-recovery system (not shown) via the pipeline 437. The catalyst is stripped in the stripping region 434 and then transported to the catalyst circulation system via the pipelines 438 and 416.

The spent catalyst from the spent catalyst receiver 408 is transported to the catalyst hopper 409 via the pipeline 417, and transported to the regenerator 407 via the pipeline 421 after the pressure release. The spent catalyst is counter-current contacted with the main air from the pipeline 227 and subjected to regeneration by coke-burning. The flue gas is transported via the pipeline 426 to the subsequent energy recovery and purification system (not shown). The regenerated catalyst is transported to the regenerated catalyst receiver 410 via the pipeline 415. The excessive heat of the regenerated catalyst is removed with the internal heat remover 414. After the heat removal, the regenerated catalyst is transported to the catalyst hopper 409 via the pipeline 418. After increasing the pressure, the regenerated catalyst is transported to the regenerated catalyst feeding tank 412 via the pipeline 422 and transported to the catalyst mixer 411 via the pipeline 423.

Fifth Specific Embodiment

Figure 5:
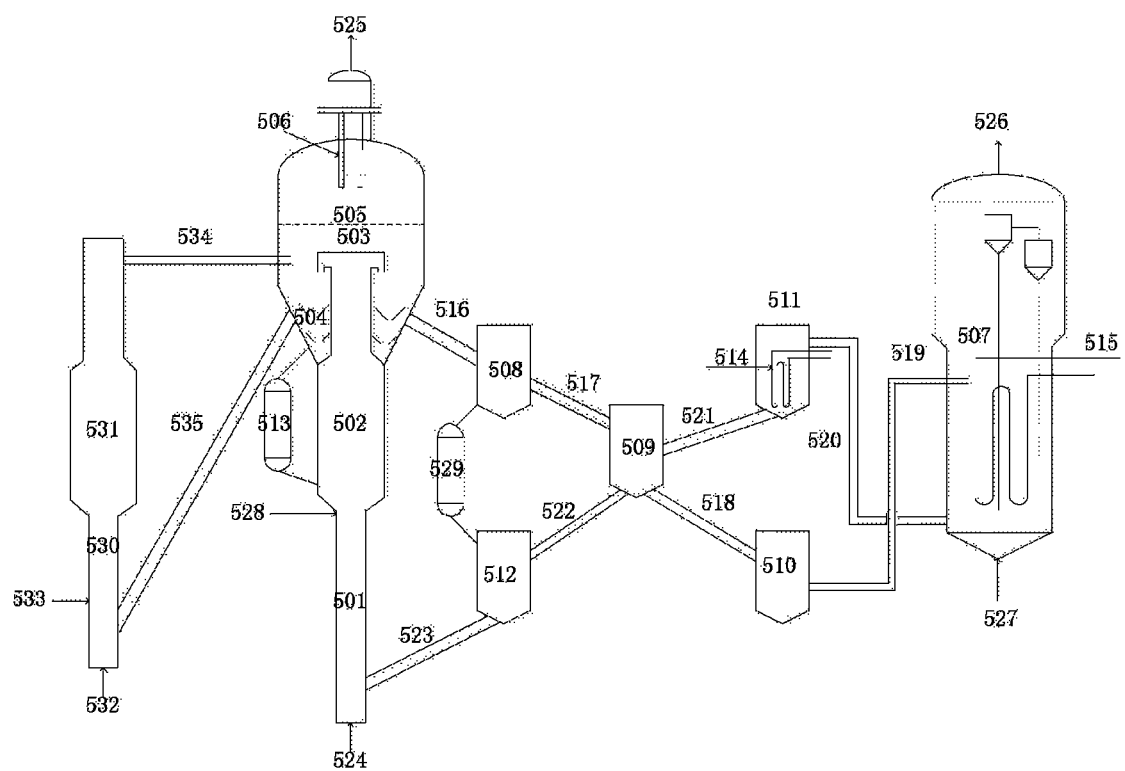
FIG. 5 is a flowchart of the process for producing light olefins from the oxygen-containing compound according to the fifth specific embodiment of the present invention

FIG. 5 is a flowchart of the process for producing light olefins from the oxygen-containing compound feedstock according to the fifth specific embodiment of the present invention.

As shown in FIG. 5, the oxygen-containing compound feedstock is transported to the riser reactor 501 of the riser-type reactor via the feeding line 524, and contacted with the catalyst from the pipeline 523 to conduct the dehydration reaction to produce olefins. After the reaction, the resulting hydrocarbon product and the catalyst are transported to the dense bed reactor 503 via the internal riser and quick separator 502. The quenching medium from the quenching medium line 528 is transported to the riser reactor 501 to control the reaction temperature. The unconverted feedstock is further contacted with the catalyst and reacted in the dense bed reactor 503. The resulting light olefins-rich hydrocarbon and the spent catalyst are transported to the sedimentation zone 505. The light olefins-rich hydrocarbon and the entrapped spent catalyst fine powder are filtered with the filter 406. After filtering, the light olefins-rich hydrocarbon is transported to a product separation-recovery system (not shown) via the pipeline 525, and the spent catalyst fine powder settles and returns to the dense bed reactor 503. The spent catalyst is stripped in the stripping region 404. After stripping, a part of the spent catalyst is transported to the spent catalyst receiver 508 via the pipeline 516, another part of the spent catalyst is transported to the first reaction zone 530 of the further riser-type reactor via the pipeline 535, and the remaining part of spent catalyst is transported to the external heat remover 513 and to the internal riser and quick separator 502 after the heat removal. The $C_4^+$ hydrocarbon obtained from the separation of the product separation-recovery system is further transported the first reaction zone 530 and the second reaction zone and necking 531 of the further riser-type reactor via the pipeline 533, and contacted with the catalyst, which is from the pipeline 535 and lifted with a pre-lifting gas via the pre-lifting line 532, to conduct the further reaction. The resulting light olefins-rich hydrocarbon and the resulting catalyst are transported to the dense bed 503 via the pipeline 534.

A part of the spent catalyst from the spent catalyst receiver 508 is transported to the external heat remover 529, and then to the regenerated catalyst feeding tank 512 after heat removal. Another part of the spent catalyst from the spent catalyst receiver 508 is transported to the catalyst hopper 509 via the pipeline 517, and then to the spent catalyst feeding tank 510 via the pipeline 518 after the pressure release, and then to the regenerator 507 via the pipeline 519. The spent catalyst is counter-current contacted with the main air from the pipeline 527 and subjected to regeneration by coke-burning. The excessive heat is removed with the internal heat remover 515. The flue gas is transported via the pipeline 526 to the subsequent energy recovery and purification system (not shown). The regenerated catalyst is transported to the regenerated catalyst receiver 511 via the pipeline 520. The excessive heat of the regenerated catalyst is removed with the internal heat remover 514. After the heat removal, the regenerated catalyst is transported to the catalyst hopper 509 via the pipeline 521. After increasing the pressure, the regenerated catalyst is transported to the regenerated catalyst feeding tank 512 via the pipeline 522. The spent catalyst from the spent catalyst receiver 508 is transported to the regenerated catalyst feeding tank 512 after the heat removal with the heat remover 529, and mixed with the regenerated catalyst. The mixed catalyst is transported to the riser reactor 501 via the pipeline 523.

Sixth Specific Embodiment

Figure 6:
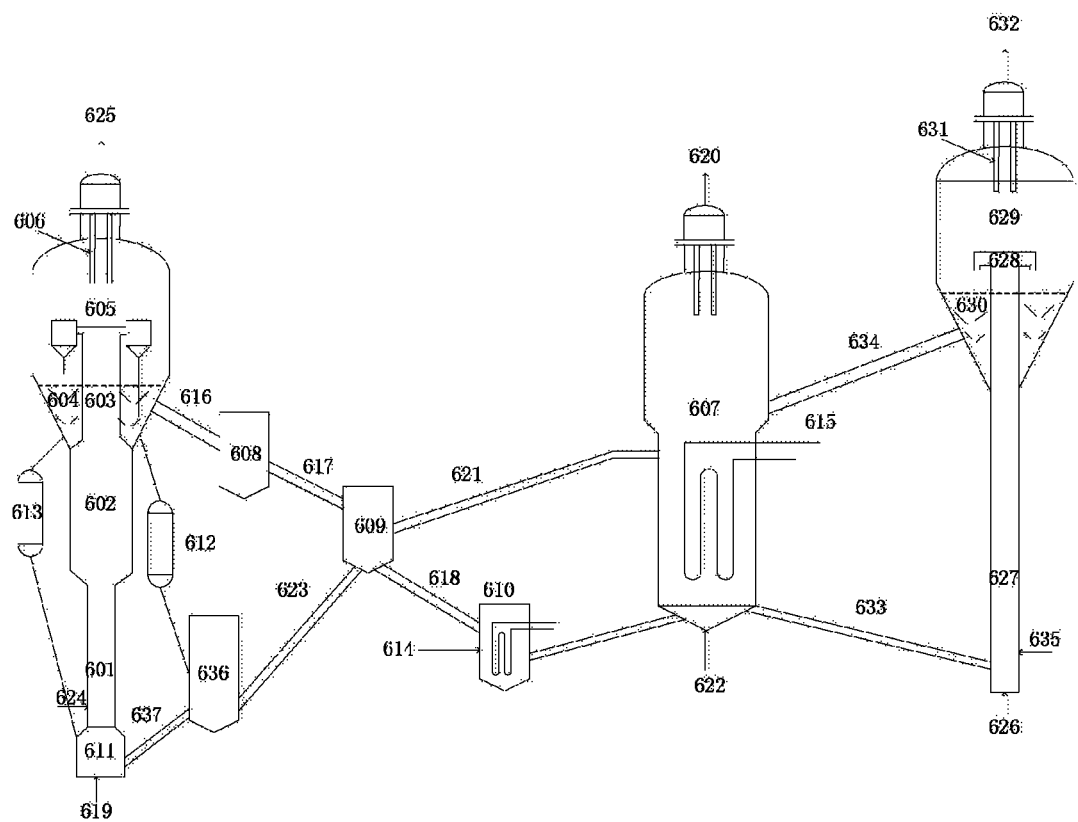
FIG. 6 is a flowchart of the process for producing light olefins from the oxygen-containing compound according to the sixth specific embodiment of the present invention

As shown in FIG. 6, the catalyst from the pipeline 637 and the spent catalyst from the external heat remover 613 are mixed in the catalyst mixer 611. The mixed catalyst is lifted with the pre-lifting gas from the pre-lifting line 619 and transported to the first reaction zone 601 of the riser-type reactor. The feedstock is transported to the first reaction zone 601 via the feeding line 624, and contacted with the catalyst from the catalyst mixer 611 to conduct the dehydration reaction to produce olefins. After the reaction, the product and the catalyst are transported to the second reaction zone 602. The unconverted feedstock is further contacted with the catalyst and reacted in the second reaction zone 602. The resulting light olefins-rich hydrocarbon and the spent catalyst are transported to the sedimentation zone 605 via the necking and quick separator 603. The light olefins-rich hydrocarbon and the entrapped spent catalyst fine powder are filtered with the filter 606. After filtering, the light olefins-rich hydrocarbon is transported to a product separation-recovery system (not shown) via the pipeline 625, and the spent catalyst fine powder settles and returns to the stripping region 604. The spent catalyst is stripped in the stripping region, a part of the spent catalyst is transported to the spent catalyst receiver 608 via the pipeline 616, another part of the spent catalyst is transported to the external heat remover 613 and then to the catalyst mixer 611 via the pipeline 624 after heat removal, and the remaining part of the spent catalyst is transported to the regenerated catalyst feeding tank 636 via the external heat remover 612 after the heat removal.

The spent catalyst from the spent catalyst receiver 608 is transported to the catalyst hopper 609 via the pipeline 617, and transported to the regenerator 607 via the pipeline 621 after the pressure release. The spent catalyst is counter-current contacted with the main air from the pipeline 622 and subjected to regeneration by coke-burning. The flue gas is transported via the pipeline 620 to the subsequent energy recovery and purification system (not shown). The excessive heat is removed with the internal heat remover 615. The regenerated catalyst is transported to the regenerated catalyst receiver 610. The excessive heat of the regenerated catalyst is removed with the internal heat remover 614. After the heat removal, the regenerated catalyst is transported to the catalyst hopper 609 via the pipeline 618. After increasing the pressure, the regenerated catalyst is transported to the regenerated catalyst feeding tank 636 via the pipeline 623 and mixed with the spent catalyst from the external heat remover 612. The mixed catalyst is transported to the catalyst mixer 611 via the pipeline 637.

The regenerated catalyst from the pipeline 633 is pre-lifted with the pre-lifting gas 626, and contacted with the $C_4^+$ olefins from the feeding line 635 to conduct the further reaction in the further riser-type reactor 627. The hydrocarbon product and the catalyst are separated with the quick separator 628 to produce the light olefins-rich hydrocarbon and the spent catalyst. The separated hydrocarbon product is subjected to the sedimentation in the sedimentation zone 629 and the filtering with filter 631. After the filtering, the hydrocarbon product is transported via the pipeline 632 to a subsequent separation system (not shown). The spent catalyst is stripped in the stripping region 630. After stripping, the spent catalyst is transported to the regenerator 607 via the pipeline 634 for regeneration.

Seventh Specific Embodiment

Figure 7:
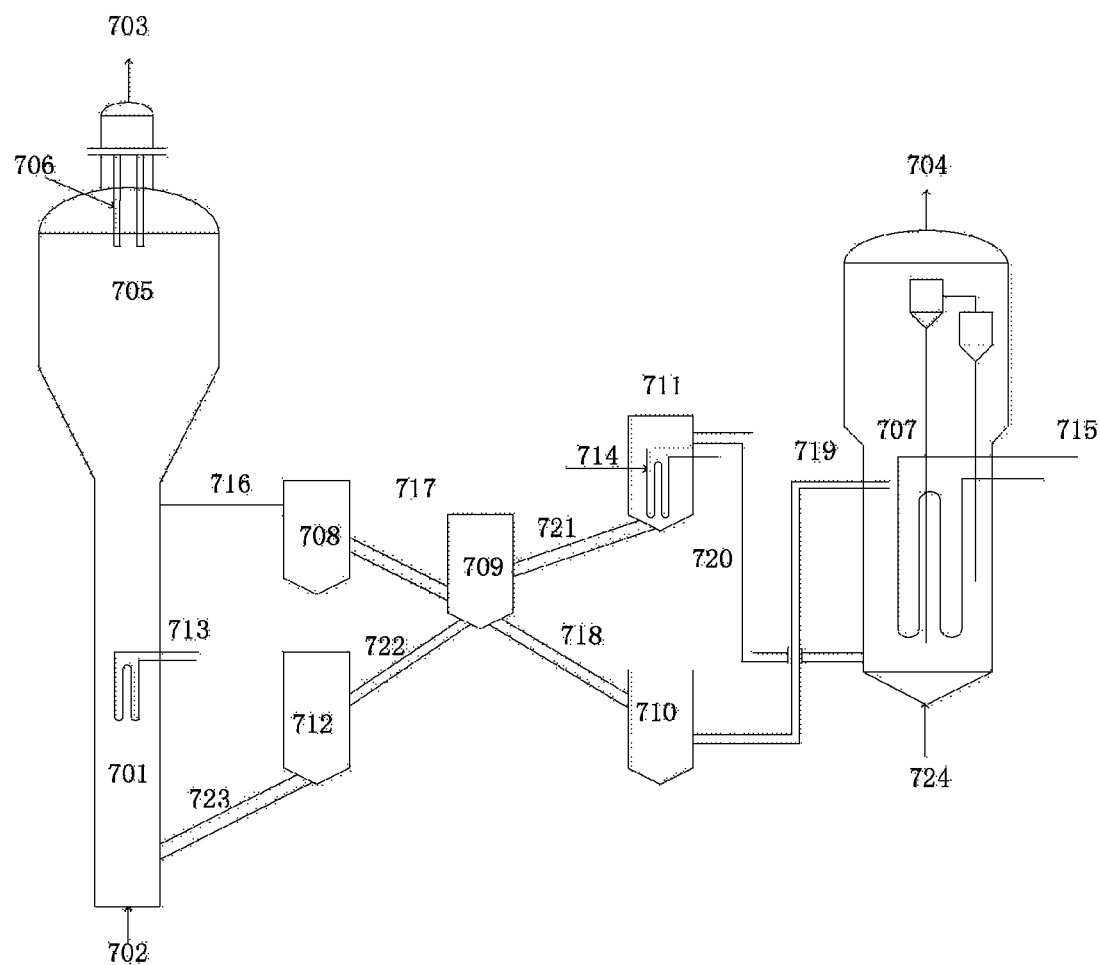
FIG. 7 is a flowchart of the process for producing light olefins from the oxygen-containing compound according to the seventh specific embodiment of the present invention The present invention can comprise other specific embodiments, and is not limited to the above seven embodiments.

FIG. 7 is a flowchart of the process for producing light olefins from the oxygen-containing compound according to the seventh specific embodiment of the present invention.

As shown in FIG. 7, the oxygen-containing compound feedstock and the diluent from the feeding line 702 are transported to the fluidized bed reactor 701, and contacted with the catalyst from the pipeline 723 to conduct the dehydration reaction to produce olefins. The excessive heat is removed with an internal heat remover 713 from the fluidized bed reactor 701. The resulting light olefins-rich hydrocarbon and a part of the resulting spent catalyst are transported to the sedimentation zone 5. After the sedimentation, the spent catalyst returns back to the fluidized bed reactor 701. The light olefins-rich hydrocarbon and the entrapped spent catalyst fine powder are filtered with the filter 706. After filtering, the light olefins-rich hydrocarbon is transported to a product separation-recovery system (not shown) via the pipeline 703 and the spent catalyst fine powder settles and returns to the fluidized bed reactor. The other part of the resulting spent catalyst is transported to the spent catalyst receiver 708 via the pipeline 716 and stripped.

The spent catalyst from the spent catalyst receiver 708 is transported to the catalyst hopper 709 via the pipeline 717, and transported to the spent catalyst feeding tank 710 via the pipeline 718, and then to the regenerator 707 via the pipeline 719. The spent catalyst is counter-current contacted with the main air from the pipeline 724 and subjected to regeneration by coke-burning. The excessive heat is removed with the internal heat remover 715. The flue gas is transported via the pipeline 704 to the subsequent energy recovery and purification system (not shown). The regenerated catalyst is transported to the regenerated catalyst receiver 711 via the pipeline 720. The excessive heat of the regenerated catalyst is removed with the internal heat remover 714. After the heat removal, the regenerated catalyst is transported to the catalyst hopper 709 via the pipeline 721. After increasing the pressure, the regenerated catalyst is transported to the regenerated catalyst feeding tank 712 via the pipeline 722, and then transported to the fluidized bed reactor 701 via the pipeline 723 after being stripped.

EXAMPLE

The following examples are used to illustrate the present invention, but the present invention is not limited to these examples.

Examples 1-6

Examples 1-6 were conducted according to the process as shown in FIG. 1 (when Examples and Comparative Examples were conducted according to the process as shown in FIG. 1, the same reactors were used) with the substantially same reaction conditions but different reaction pressures and weight hourly space velocities. The reaction feedstock, the catalyst, the reaction conditions and the product yield were listed in Table 1.

It could be seen from Examples 1-6 that the technical solution of the present invention, i.e. increasing the reaction pressure and simultaneously and correspondingly increasing the WHSV, and maintaining the substantially equivalent other reaction conditions, could accomplish the yield of light olefins as high as 84.9%.

Example 7-8

Examples 7-8 were conducted according to the process as shown in FIG. 1. Compared with Example 4, in Examples 7-8, when the reaction pressure was increased, the WHSV was not correspondingly increased, and other operation conditions were substantially kept as the same. The reaction feedstock, the catalyst, the reaction conditions and the product yield were listed in Table 2.

It could be seen from Example 4, Example 7 and Example 8 that compared with Example 4, if only increasing the reaction pressure without correspondingly increasing the WHSV under the substantially same other reaction conditions, the output and yield of light olefins would decrease, wherein the yield of light olefins decreased from 84.3% of Example 4 to 82.9% of Example 8; the output of light olefins decreased from 3.73 kg/h of Example 4 to 2.64 kg/h of Example 8.

Example 9

Example 9 was conducted according to the process as shown in FIG. 1, Compared with Example 3, the operation conditions were substantially kept as the same with only changing the carbon content of the catalyst at the inlet of the reactor (Carbon content of the catalyst at the inlet of the reactor refers to the carbon content of the catalyst at the inlet of the reactor, which catalyst has not been contacted with the feedstock). The reaction feedstock, the catalyst, the reaction conditions and the product yield were listed in Table 2.

It could be seen from Example 3 and Example 9 that compared with Example 3, if the reaction pressure and the weight hourly space velocity were substantially kept as the same, when the carbon content of the catalyst at the inlet of the reactor decreased from 7.3% to 4.5%, the output of light olefins decreased from 3.84 kg/h to 3.58 kg/h; the yield of light olefins decreased from 84.9% to 84.3%; the mass ratio of ethylene to propylene increased.

Example 10

Example 10 was conducted according to the process as shown in FIG. 3. The reaction feedstock, the catalyst, the reaction conditions and the product yield were listed in Table 2.

It could be seen from Example 10 that the yield of light olefins was 93.3%, the output of light olefin was 4.03 kg/h.

Example 11

Example 11 was conducted according to the process as shown in FIG. 7. The reaction feedstock (feedstock=ethanol), the catalyst, the reaction conditions and the product yield were listed in Table 2. It could be seen from Example 11 that the yield of light olefins was 82.8%, the output of light olefin was 3.26 kg/h.

Example 12

Example 12 was conducted according to the process as shown in FIG. 2. The reaction feedstock, the catalyst, the reaction conditions and the product yield were listed in Table 4.

Example 12 was a technical solution in which both the production of light olefins and the production of gasoline were increased. It could be seen from Example 12 that the propylene yield was 65.9%, the gasoline yield was 25.3%, the propylene output was 1.98 kg/h, the gasoline output was 0.76 kg/h.

Comparative Examples 1-6

Comparative Examples 1-6 were conducted with the same reactors, feedstocks and catalysts as those of Examples 1-10, and were conducted according to the process as shown in FIG. 1. Compared with Examples 1-10, Comparative Example 1 was conducted in a conventional condition for producing light olefins from methanol, wherein the carbon content of the catalyst at the inlet of the reactor is remarkably lower, and the reaction pressure and the weight hourly space velocity were remarkably lower than those of the present invention; for Comparative Examples 2-6, only the reaction pressure and the WHSV were changed, and other operation conditions were substantially kept as the same with those of Examples 1-10. The reaction feedstock, the catalyst, the reaction conditions and the product yield of Comparative Examples 1-6 were listed in Table 3.

Comparative Example 1 was conducted in a conventional condition for producing light olefins from methanol. Comparative Example 2 was only different from Comparative Example 1 in the carbon content of the catalyst at the inlet of the reactor. Compared with Comparative Example 1, the carbon content of the catalyst at the inlet of the reactor was increased from 1.5% of Comparative Example 1 to 7.2% of Comparative Example 2, the output of light olefins was decreased from 0.47 kg/h of Comparative Example 1 to 0.43 kg/h of Comparative Example 2; the conversion rate was decreased from 100% of Comparative Example 1 to 80.2% of Comparative Example 2.

Except for the reaction pressure and the weight hourly space velocity, Comparative Example 2 had the substantially same carbon content of the catalyst at the inlet of the reactor as Examples 1-8. Compared with Comparative Example 2, Examples 1-8 had the substantially same or slightly higher light olefins yields and the remarkably higher light olefins outputs. For example, the yield of light olefins was increased from 79.2% of Comparative Example 2 to 84.9% of Example 3; the output of light olefins was increased from 0.43 kg/h of Comparative Example 2 to 3.84 kg/h of Example 3, and the increasing amplitude was as high as 793.02%.

For Comparative Example 3 and Example 3, except the weight hourly space velocity, the other reaction conditions were kept as the same. Comparative Example 3 had a remarkably higher weight hourly space velocity than Example 3. Compared with Comparative Example 3, after using the present invention, the output of light olefins was increased from 0.46 kg/h of Comparative Example 3 to 3.84 kg/h of Example 3, and the increasing amplitude was as high as 734.78%; the yield of light olefins was increased from 82.9% of Comparative Example 3 to 84.9% of Example 3.

For Comparative Example 4 and Example 2, except for the reaction pressure, the other reaction conditions were kept as the same. Comparative Example 4 had a remarkably lower reaction pressure than Example 2. Compared with Comparative Example 4, after using the present invention, the output of light olefins was increased from 0.44 kg/h of Comparative Example 4 to 2.54 kg/h of Example 2, and the increasing amplitude was as high as 477.27%; the yield of light olefins was increased from 79.4% of Comparative Example 4 to 84.4% of Example 2.

For Comparative Example 5 and Example 2, except for the weight hourly space velocity, the other reaction conditions were kept as the same. Comparative Example 5 had a remarkably lower weight hourly space velocity than Example 2. Compared with Comparative Example 5, after using the present invention, the output of light olefins was increased from 0.43 kg/h of Comparative Example 5 to 2.54 kg/h of Example 2, and the increasing amplitude was as high as 490.70%; the yield of light olefins was increased from 75.3% of Comparative Example 5 to 84.4% of Example 2.

For Comparative Example 6 and Example 1, except for the reaction pressure, the other reaction conditions were kept as the same. Comparative Example 6 had a remarkably higher reaction pressure than Example 1. Compared with Comparative Example 6, after using the present invention, the output of light olefins was increased from 0.33 kg/h of Comparative Example 6 to 1.11 kg/h of Example 1, and the increasing amplitude was as high as 236.36%; the yield of light olefins was increased from 33.4% of Comparative Example 6 to 83.7% of Example 1.

TABLE 1

|  | Example 1 | Example 2 | Example 3 | Example 4 | Example 5 | Example 6 |
|---|---|---|---|---|---|---|
| The reaction feedstock (the mass fraction of the oxygen-containing compound >98 wt %) | methanol | methanol | methanol | methanol | methanol | methanol |
| Catalyst (Sinopec Catalyst Co., Ltd. Qilu Division) | SAPO-34 zeolite catalyst | SAPO-34 zeolite catalyst | SAPO-34 zeolite catalyst | SAPO-34 zeolite catalyst | SAPO-34 zeolite catalyst | SAPO-34 zeolite catalyst |
| Reaction conditions | | | | | | |
| Reaction temperature, ° C. | 450 | 450 | 450 | 450 | 450 | 450 |
| Reaction pressure, MPa | 0.7 | 0.8 | 1.2 | 2.5 | 5.0 | 7 |
| WHSV, $h^{-1}$ | 10 | 22 | 30 | 41 | 93 | 163 |
| Carbon content of the catalyst at the inlet of the reactor, wt % | 7.2 | 7.2 | 7.3 | 7.3 | 7.2 | 7.3 |
| Regeneration conditions | | | | | | |
| Regeneration temperature, ° C. | 580 | 580 | 570 | 570 | 580 | 580 |
| Regeneration pressure, MPa | 0.4 | 0.4 | 0.4 | 0.4 | 0.6 | 0.4 |
| The feedstock amount (as pure), kg/h | 3.02 | 6.90 | 10.35 | 17.97 | 43.14 | 65.43 |
| Mol (feedstock)/mol (diluent) | 5.1 | 5.1 | 5.1 | 5.1 | 5.1 | 5.1 |
| The conversion rate of the feedstock, wt % | 100 | 100 | 100 | 56.3 | 23.2 | 14.7 |
| The output of light olefins, kg/h | | | | | | |
| Ethylene | 0.56 | 1.27 | 1.89 | 1.75 | 1.57 | 1.48 |
| Propylene | 0.55 | 1.27 | 1.95 | 1.98 | 2.09 | 1.95 |
| Butylene | 0.11 | 0.25 | 0.39 | 0.38 | 0.38 | 0.39 |
| Ethylene + propylene | 1.11 | 2.54 | 3.84 | 3.73 | 3.66 | 3.43 |
| The yield of light olefins*, wt % | | | | | | |
| Ethylene | 42.3 | 42.1 | 41.8 | 39.6 | 35.8 | 35.2 |
| Propylene | 41.4 | 42.3 | 43.1 | 44.7 | 47.8 | 46.3 |
| Butylene | 8.1 | 8.4 | 8.6 | 8.7 | 8.6 | 9.3 |
| Ethylene + propylene | 83.7 | 84.4 | 84.9 | 84.3 | 83.6 | 81.5 |

Yield = the output of the product/the sum of the output of the hydrocarbon products except the oxygen-containing compound * 100.

TABLE 2

|  | Example 7 | Example 8 | Example 9 | Example 10 | Example 11 |
|---|---|---|---|---|---|
| The reaction feedstock (the mass fraction of the oxygen-containing compound >98 wt %) | methanol | methanol | methanol | methanol | ethanol |
| Catalyst (Sinopec Catalyst Co., Ltd. Qilu Division) | SAPO-34 zeolite catalyst | SAPO-34 zeolite catalyst | SAPO-34 zeolite catalyst | SAPO-34 zeolite catalyst | SAPO-34 zeolite catalyst |
| Reaction conditions | | | | | |
| Reaction temperature, ° C. | 450 | 450 | 430 | 450 | 470 |
| Reaction pressure, MPa | 2.8 | 3.2 | 1.5 | 2.3 | 1 |
| WHSV, $h^{-1}$ | 36 | 26 | 26 | 40 | 25 |
| Carbon content of the catalyst at the inlet of the reactor, wt % | 7.3 | 7.2 | 4.5 | 10.2 | 8.2 |
| Regeneration conditions | | | | | |
| Regeneration temperature, ° C. | 590 | 590 | 550 | 650 | 600 |
| Regeneration pressure, MPa | 0.4 | 0.4 | 0.3 | 0.6 | 0.3 |

TABLE 2-continued

|  | Example 7 | Example 8 | Example 9 | Example 10 | Example 11 |
| --- | --- | --- | --- | --- | --- |
| The feedstock amount (as pure), kg/h | 16.10 | 11.50 | 9.71 | 16.54 | 8.63 |
| Mol (feedstock)/mol (diluent) | 5.1 | 5.1 | 5.1 | 5.1 | 3.5 |
| The conversion rate of the feedstock, wt % | 58.7 | 63.4 | 100 | 59.9 | 100 |
| The output of light olefins, kg/h | | | | | |
| Ethylene | 1.60 | 1.20 | 2.10 | 2.26 | 1.36 |
| Propylene | 1.86 | 1.44 | 1.48 | 1.77 | 1.90 |
| Butylene | 0.37 | 0.29 | 0.36 | 0.00 | 0.35 |
| Ethylene + propylene | 3.46 | 2.64 | 3.58 | 4.03 | 3.26 |
| The yield of light olefins*, wt % | | | | | |
| Ethylene | 38.7 | 37.7 | 49.5 | 52.3 | 34.6 |
| Propylene | 45.0 | 45.2 | 34.8 | 41.0 | 48.2 |
| Butylene | 8.9 | 9.2 | 8.6 | 0 | 9 |
| Ethylene + propylene | 83.7 | 82.9 | 84.3 | 93.3 | 82.8 |

*Yield = the output of the product/the sum of the output of the hydrocarbon products except the oxygen-containing compound * 100.

TABLE 3

|  | Comparative Example 1 | Comparative Example 2 | Comparative Example 3 | Comparative Example 4 | Comparative Example 5 | Comparative Example 6 |
| --- | --- | --- | --- | --- | --- | --- |
| The reaction feedstock (the mass fraction of the oxygen-containing compound >98 wt %) | methanol | methanol | methanol | methanol | methanol | methanol |
| Catalyst (Sinopec Catalyst Co., Ltd. Qilu Division) | SAPO-34 zeolite catalyst | SAPO-34 zeolite catalyst | SAPO-34 zeolite catalyst | SAPO-34 zeolite catalyst | SAPO-34 zeolite catalyst | SAPO-34 zeolite catalyst |
| Reaction conditions | | | | | | |
| Reaction temperature, ° C. | 450 | 450 | 450 | 450 | 450 | 450 |
| Reaction pressure, MPa | 0.12 | 0.12 | 1.5 | 0.12 | 0.9 | 12 |
| WHSV, h$^{-1}$ | 5 | 5 | 352 | 22 | 1 | 8 |
| Carbon content of the catalyst at the inlet of the reactor, wt % | 1.2 | 7.2 | 7.2 | 7.2 | 7.3 | 7.2 |
| Regeneration conditions | | | | | | |
| Regeneration temperature, ° C. | 580 | 580 | 570 | 570 | 580 | 570 |
| Regeneration pressure, MPa | 0.4 | 0.4 | 0.4 | 0.4 | 0.4 | 0.4 |
| The feedstock amount (as pure), kg/h | 1.38 | 1.55 | 34.51 | 4.31 | 1.29 | 12.94 |
| Mol (feedstock)/mol (diluent) | 5.1 | 5.1 | 5.1 | 5.1 | 5.1 | 5.1 |
| The conversion rate of the feedstock, wt % | 100 | 80.2 | 3.7 | 29.5 | 100 | 17.3 |
| The output of light olefins, kg/h | | | | | | |
| Ethylene | 0.24 | 0.20 | 0.20 | 0.20 | 0.19 | 0.12 |
| Propylene | 0.23 | 0.23 | 0.26 | 0.24 | 0.24 | 0.21 |
| Butylene | 0.05 | 0.05 | 0.05 | 0.05 | 0.05 | 0.16 |
| Ethylene + propylene | 0.47 | 0.43 | 0.46 | 0.44 | 0.43 | 0.33 |

TABLE 3-continued

|  | Comparative Example 1 | Comparative Example 2 | Comparative Example 3 | Comparative Example 4 | Comparative Example 5 | Comparative Example 6 |
|---|---|---|---|---|---|---|
| The yield of light olefins*, wt % | | | | | | |
| Ethylene | 40.5 | 36.6 | 36.7 | 36.6 | 33.7 | 12.3 |
| Propylene | 38.1 | 42.6 | 46.2 | 42.8 | 41.6 | 21.1 |
| Butylene | 8.6 | 8.6 | 8.2 | 8.4 | 9.2 | 16.0 |
| Ethylene + propylene | 78.6 | 79.2 | 82.9 | 79.4 | 75.3 | 33.4 |

*Yield = the output of the product/the sum of the output of the hydrocarbon products except the oxygen-containing compound * 100.

TABLE 4

|  | Example 12 |
|---|---|
| The reaction feedstock (the mass fraction of the oxygen-containing compound >98 wt %) | dimethylether |
| Catalyst (Sinopec Catalyst Co., Ltd. Qilu Division) | ZSM-5 zeolite catalyst |
| Reaction conditions | |
| Reaction temperature, ° C. | 500 |
| Reaction pressure, MPa | 1.5 |
| WHSV, $h^{-1}$ | 19 |
| Carbon content of the catalyst at the inlet of the reactor, wt % | 10.2 |
| Regeneration conditions | |
| Regeneration temperature, ° C. | 650 |
| Regeneration pressure, MPa | 0.2 |
| The feedstock amount (as pure), kg/h | 6.56 |
| Mol (feedstock)/mol (diluent) | 1.6 |
| The conversion rate of the feedstock, wt % | 100 |
| The output of the major products, kg/h | |
| Ethylene | 0.12 |
| Propylene | 1.98 |
| Gasoline | 0.76 |
| Ethylene + propylene | 2.10 |
| The yield of the major products*, wt % | |
| Ethylene | 4.1 |
| Propylene | 65.9 |
| Gasoline | 25.3 |

Yield = the output of the product/the sum of the output of the hydrocarbon products except the oxygen-containing compound * 100.

Example I

Example I was performed according to the process as shown in FIG. 1, wherein the reaction feedstock, the catalyst, the reaction conditions and the product yield were listed in Table I.

Example II

Example II was performed according to the process as shown in FIG. 3, wherein the reaction feedstock, the catalyst, the reaction conditions and the product yield were listed in Table I.

Example III

Example III was performed according to the process as shown in FIG. 2, wherein the reaction feedstock, the catalyst, the reaction conditions and the product yield were listed in Table II.

It could be seen from Table I that the present process had the yields of ethylene and propylene higher than those of the prior art. It could be seen from Table II that the present process had the yields of propylene and gasoline of 65.9% and 25.3%, which were higher than those of the prior art. Since the reaction system of the present invention had a higher pressure than the existing industrial plants, therefore under the same other reaction conditions, the reaction system of the present invention would have a higher feedstock throughput than the existing industrial plant.

TABLE I

|  | Example I | Example II |
|---|---|---|
| The reaction feedstock (the mass fraction of the oxygen-containing compound feedstock >98 wt %) | Industrial methanol | Industrial methanol |
| Catalyst (Sinopec Catalyst Co., Ltd. Qilu Division) | SAPO-34 zeolite catalyst | SAPO-34 zeolite catalyst |
| The reaction conditions of the riser-type reactor | | |
| Temperature, ° C. | 430 | 450 |
| Pressure, MPa | 1.5 | 2.3 |
| The regeneration conditions of the regenerator | | |
| Regeneration pressure, MPa | 0.3 | 0.6 |
| Regeneration temperature, ° C. | 550 | 650 |
| Regenerated catalyst content (preset), wt % | 0.2 | 0.4 |
| The reaction conditions of the further riser-type reactor | | |
| Temperature, ° C. | — | 450 |
| Pressure, MPa | — | 2.3 |
| Product yield | | |
| Ethylene, % | 49.5 | 52.3 |
| Propylene, % | 34.8 | 41.0 |
| Butylene, % | 8.6 | 0.0 |

TABLE II

|  | Example III |
|---|---|
| The reaction feedstock (the mass fraction of the oxygen-containing compound feedstock >98 wt %) | Industrial dimethylether |
| Catalyst (Sinopec Catalyst Co., Ltd. Qilu Division) | ZSM-5 zeolite catalyst |
| The reaction conditions of the riser-type reactor | |
| Temperature, ° C. | 500 |
| Pressure, MPa | 1.5 |
| The regeneration conditions of the regenerator | |
| Regeneration pressure, MPa | 0.2 |
| Regeneration temperature, ° C. | 650 |
| Regenerated catalyst content (preset), wt % | 0.4 |
| Product yield | |
| Ethylene, % | 4.1 |
| Propylene, % | 65.9 |
| Gasoline, % | 25.3 |

The invention claimed is:

1. A process for producing light olefins, comprising:
contacting a feedstock comprising an oxygen-containing compound and a first catalyst in a first reactor to conduct a dehydration reaction;
obtaining from the first reactor a first effluent comprising light olefins and a first spent catalyst;
transferring at least a part of the first spent catalyst from the first reactor into a pressure switch device;
depressurizing the pressure switch device;
transferring the at least a part of the first spent catalyst from the depressurized pressure switch device to a first regenerator;
regenerating the at least a part of the first spent catalyst in the first regenerator to obtain a first regenerated catalyst;
transferring at least a part of the first regenerated catalyst from the first regenerator into the pressure switch device;
pressurizing the pressure switch device;
transferring the at least a part of the first regenerated catalyst from the pressurized pressure switch device to the first reactor,
wherein the oxygen-containing compound is selected from the group consisting of methanol, ethanol, dimethylether, diethylether, methyl-ethyl-ether, methylene carbonate, methyl formate, and mixtures thereof,
wherein, in absolute pressure, a reaction pressure P of the dehydration reaction in the first reactor is in a range of 0.75 MPa to 3.5 MPa, and is at least 0.4 MPa higher than a regeneration pressure in the first regenerator, wherein a weight hourly space velocity H in the first reactor is in a range of 8 $h^{-1}$ to 150 $h^{-1}$, and wherein the pressure switch device is a catalyst hopper or a lock hopper.

2. The process according to claim 1, wherein the reaction pressure P is in a range of 0.8 MPa to 3 MPa, and is at least 0.5 MPa than the regeneration pressure in the first regenerator.

3. The process according to claim 1, further comprising a step of separating the light olefins from the first effluent to obtain a stream containing C4+ hydrocarbon, and optionally further comprising the steps of:
contacting the stream containing C4+ hydrocarbon and a second catalyst in a second reactor to produce a second effluent containing light olefins and a second spent catalyst,
regenerating at least a part of the second spent catalyst in the first regenerator to obtain a second regenerated catalyst, and
circulating at least a part of the second regenerated catalyst to the first reactor, or the second reactor, or both.

4. The process according to claim 3, wherein the first catalyst and the second catalyst are identical or different from each other, each independently selected from the group consisting of zeolite catalysts, aluminosilicophosphate zeolite catalysts, aluminosilicate zeolite catalysts, and combinations thereof.

5. The process according to claim 2, wherein the first regenerator is operated at a reaction temperature of 450-850° C. under a reaction pressure of 0.35-3.1 MPa in an oxygen-containing atmosphere.

6. The process according to claim 3, wherein each of the first spent catalyst, the second spent catalyst, the first regenerated catalyst, and the second regenerated catalyst is obtained by separation through filtration.

7. The process according to claim 1, wherein the first reactor is a riser reactor.

8. The process according to claim 3, further comprising a step of circulating at least a part of the first spent catalyst to the first reactor, or the second reactor, or both.

9. The process according to claim 3, wherein the first catalyst, the second catalyst, or both the first catalyst and the second catalyst have a carbon content of 3-25 wt %.

10. The process according to claim 1, further comprising a step of circulating an incompletely-reacted oxygen-containing compound feedstock to the dehydration reaction.

11. The process according to claim 2, further comprising:
separating light olefins and the first spent catalyst from the first effluent in a hydrocarbon-catalyst separation zone, introducing the light olefins into a product separation-recovery system, stripping the first spent catalyst in a stripping region of the riser reactor, withdrawing the first spent catalyst from the riser reactor and transporting the first spent catalyst to a spent catalyst receiver.

12. The process according to claim 1, wherein the reaction pressure P is in a range of 1 MPa to 3 MPa, and is at least 0.6 MPa higher than the regeneration pressure in the first regeneration reactor.

13. The process according to claim 2, wherein the reaction pressure P is in a range of 1.2 MPa to 2.8 MPa, and is at least 0.7 MPa higher than the regeneration pressure in the first regenerator.

14. The process according to claim 1, wherein a weight hourly space velocity H in the first reactor is in a range of 10 $h^{-1}$ to 100 $h^{-1}$.

* * * * *